US006451539B2

(12) United States Patent
Innis et al.

(10) Patent No.: US 6,451,539 B2
(45) Date of Patent: Sep. 17, 2002

(54) EXPRESSION VECTORS, TRANSFECTION SYSTEMS, AND METHOD OF USE THEREOF

(75) Inventors: Michael Innis, Moraga; Elizabeth M. Scott, Sonoma, both of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/748,061

(22) Filed: Dec. 22, 2000

Related U.S. Application Data

(62) Division of application No. 09/475,460, filed on Dec. 30, 1999, now Pat. No. 6,316,253.
(60) Provisional application No. 60/162,930, filed on Nov. 1, 1999.

(51) Int. Cl.[7] .......................... C12Q 1/68; G01N 33/53; C12N 15/63; C12N 15/85; C12N 5/06; C12P 21/06; C07H 21/04
(52) U.S. Cl. .......................... 435/6; 435/7.1; 435/69.1; 435/320.1; 435/325; 435/455; 536/23.1; 536/24.1
(58) Field of Search .............................. 435/69.1, 320.1, 435/325, 6, 7.1, 455; 536/23.1, 24.1, 24.2

(56) References Cited

U.S. PATENT DOCUMENTS

| 4,959,317 A | 9/1990 | Sauer ........................ 435/462 |
| 5,679,546 A | 10/1997 | Ko et al. .................... 435/69.2 |
| 5,928,914 A | 7/1999 | Leboulch et al. ............ 435/456 |

FOREIGN PATENT DOCUMENTS

| EP | 919619 A2 | 6/1999 |
| WO | WO 95/24485 | 9/1995 |
| WO | WO 97/31115 | 8/1997 |
| WO | WO 97/48370 | 12/1997 |
| WO | WO 98/34640 | 8/1998 |
| WO | WO 98/41645 | 9/1998 |
| WO | WO 98/41398 | 8/1999 |

OTHER PUBLICATIONS

Blazquez, et al., "Mutations in the aphA–2 Gene of Transposon Tn5 Mapping Within the Regions Highly Conserved in Aminoglycoside–Phosphotransferases Strongly Reduce Aminoglycoside Resistance," *Molecular Microbiology* 5(6):1511–1518 (1991).

Bullerjahn, et al., "Site–Directed Deletion Mutants of a Carobxyl–Terminal Region of Human Dihydrofolate Reductase," *The Journal of Biologiccal Chemistry* 267(2):864–870 (1992).

Gilbert, D.M., et al., "Bovine Papilloma Virsu Plasmids Replicate Randomly in Mouse Fibroblast Throughout S Phase of the Cell Cycle," *Cell* 50:59–68 (1987).

Gossen, et al., "Transcriptional Activation by Tetracyclines in Mammalian Cells," *Science* 268:1766–1769 (1995).

Higgins, et al., "A Soluble Chimeric Complement Inhibitory Protein That Possessses Both Decay–Accelerating and Factor I Cofactor Activities," *J. Immunology* 158(6):2872–2881 (1997).

Lebkowski, J.S., et al., "Transfected DNA Is Mutated in Monkey, Mouse, and Human Cells," *Mol. Cell. Biol.* 4(10):1951–1960 (1984).

Ravnan, J.–B., et al., "Random–Choice Replication of Extrachomosomal Bovine Papillomavirus (BPV) Molecules in Heterogeneous, Clonally Derived BPV–Infected Cell Lines," *J. Virol.* 66(12):6946–6952 (1992).

Schernthaner et al., "Endosperm–Specific Activity of a Zein Gene Promoter in Transgenic Tobacco Plants," *EMBO Journal* 7(5):1249–1255 (1988).

Seidman, "Intermolecular Homologous Recombination Between Transfected Sequences is Mammalian Celss is Primarily Nonconservative," *Molecular and Cellular Biology* 7(10):3561–3565 (1987).

Simonsen, et al., "Isolation and Expression of an Altered Mouse Dihydrofolate Reductase cDNA," *Proc. Natl. Acad. Sci. USA* 80:2495–2499 (1983).

Yates, J., et al., "A cis–acting Element From the Epstein–Barr Viral Genome That Permits Stable Replication of Recombinant Plasmids in Latently Infected Cells," *Proc. Natl. Acad. Sci. USA* 81:3806–3810 (1984).

Yates, J., et al., "Stable Replication of Plasmids Derived From Epstein–Barr Virus in Various Mammalian Cells," *Nature* (London) 313:812–815 (1985).

Yenofsky et al., "A Mutant Neomycin Phosphotransferase II Gene Reduces the Resistance of Transformants to Antibiotic Selection Pressure," *Proc. Natl. Acad. Sci. U.S.A.* 87:3435–3439 (1990).

*Primary Examiner*—David Guzo
*Assistant Examiner*—Katharine F Davis
(74) *Attorney, Agent, or Firm*—Robert P. Blackburn; Dahna S. Pasternak; Anne S. Dollard

(57) ABSTRACT

Expression vectors and transfection systems providing high expression of a desired polypeptide are provided. Also provided are methods of using the expression vectors and transfection systems and mammalian cells modified by these compositions and methods.

23 Claims, 8 Drawing Sheets

CAB2 with splice site deletions
(lower case represents original sequence)

```
      MetGluProProGlyArgArgGluCysProPheProSerTrpArgPheProGly
  3   GGCCGCATGGAGCCTCCCGGCCGCCGCGAGTGTCCCTTTCCTTCCTGGCGCTTTCCTGGG

LeuLeuLeuAlaAlaMetValLeuLeuLeuTyrSerPheSerAspAlaCysGluGluPro
 63   TTGCTTCTGGCGGCCATGGTGTTGCTGCTGTACTCCTTCTCCGATGCCTGTGAGGAGCCA

ProThrPheGluAlaMetGluLeuIleGlyLysProLysProTyrTyrGluIleGlyGlu
                                  C   G
123   CCAACATTTGAAGCTATGGAGCTCATtGGtAAACCAAAACCCTACTATGAGATTGGTGAA
                                  Donor 1

ArgValAspTyrLysCysLysLysGlyTyrPheTyrIleProProLeuAlaThrHisThr
183   CGAGTAGATTATAAGTGTAAAAAGGATACTTCTATATACCTCCTCTTGCCACCCATACT

IleCysAspArgAsnHisThrTrpLeuProValSerAspAspAlaCysTyrArgGluThr
243   ATTTGTGATCGGAATCATACATGGCTACCTGTCTCAGATGACGCCTGTTATAGAGAAACA

CysProTyrIleArgAspProLeuAsnGlyGlnAlaValProAlaAsnGlyThrTyrGlu
303   TGTCCATATATACGGGATCCTTTAAATGGCCAAGCAGTCCCTGCAAATGGGACTTACGAG

PheGlyTyrGlnMetHisPheIleCysAsnGluGlyTyrTyrLeuIleGlyGluGluIle
363   TTTGGTTATCAGATGCACTTTATTTGTAATGAGGGTTATTACTTAATTGGTGAAGAAATT

LeuTyrCysGluLeuLysGlySerValAlaIleTrpSerGlyLysProProIleCysGlu
                                              A A     C
423   CTATATTGTGAACTTAAAGGATCAGTAGCAATTTGGAGCGGtAAgCCCCCaATATGTGAA
                                                  Donor 2

LysValLeuCysThrProProLysIleLysAsnGlyLysHisThrPheSerGluVal
483   AAGGTTTTGTGTACACCACCTCCAAAAATAAAAAATGGAAAACACACCTTTAGTGAAGTA

GluValPheGluTyrLeuAspAlaValThrTyrSerCysAspProAlaProGlyProAsp
543   GAAGTATTTGAGTATCTTGATGCAGTAACTTATAGTTGTGATCCTGCACCTGGACCAGAT

ProPheSerLeuIleGlyGluSerThrIleTyrCysGlyAspAsnSerValTrpSerArg
603   CCATTTTCACTTATTGGAGAGAGCACGATTTATTGTGGTGACAATTCAGTGTGGAGTCGT

AlaAlaProGluCysLysValValLysCysArgPheProValValGluAsnGlyLysGln
663   GCTGCTCCAGAGTGTAAAGTGGTCAAATGTCGATTTCCAGTAGTCGAAAATGGAAAACAG
                                                                ^
722   ECORV,
```

FIG. 1A

```
     IleSerGlyPheGlyLysLysPheTyrTyrLysAlaThrValMetPheGluCysAspLys
 723 ATATCAGGATTTGGAAAAAAATTTTACTACAAAGCAACAGTTATGTTTGAATGCGATAAG

GlyPheTyrLeuAspGlySerAspThrIleValCysAspSerAsnSerThrTrpAspPro
 783 GGTTTTTACCTCGATGGCAGCGACACAATTGTCTGTGACAGTAACAGTACTTGGGATCCC

ProValProLysCysLeuLysValSerThrAspCysGlyLeuProProAspValProAsn
 843 CCAGTTCCAAAGTGTCTTAAAGTGTCGACTGACTGTGGCCTTCCCCCAGATGTACCTAAT

AlaGlnProAlaLeuGluGlyArgThrSerPheProGluAspThrValIleThrTyrLys
 903 GCCCAGCCAGCTTTGGAAGGCCGTACAAGTTTTCCCGAGGATACTGTAATAACGTACAAA

CysGluGluSerPheValLysIleProGlyGluLysAspSerValIleCysLeuLysGly
 963 TGTGAAGAAAGCTTTGTGAAAATTCCTGGCGAGAAGGACTCAGTGATCTGCCTTAAGGGC

SerGlnTrpSerAspIleGluGluPheCysAsnArgSerCysGluValProThrArgLeu
1023 AGTCAATGGTCAGATATTGAAGAGTTCTGCAATCGTAGCTGCGAGGTGCCAACAAGGCTA

AsnSerAlaSerLeuLysGlnProTyrIleThrGlnAsnTyrPheProValGlyThrVal
                                                C   C   T
1083 AATTCTGCATCCCTCAAACAGCCTTATATCACTCAGAATTAtTTtCCaGTCGGTACTGTT
                                              Acceptor 1

ValGluTyrGluCysArgProGlyTyrArgArgGluProSerLeuSerProLysLeuThr
1143 GTGGAATATGAGTGCCGTCCAGGTTACAGAAGAGAACCTTCTCTATCACCAAAACTAACT

CysLeuGlnAsnLeuLysTrpSerThrAlaValGluPheCysLysLysLysSerCysPro
1203 TGCCTTCAGAATTTAAAATGGTCCACAGCAGTCGAATTTTGTAAAAAGAAATCATGCCCT

AsnProGlyGluIleArgAsnGlyGlnIleAspValProGlyGlyIleLeuPheGlyAla
1263 AATCCGGGAGAAATACGAAATGGTCAGATTGATGTACCAGGTGGCATATTATTTGGTGCA

ThrIleSerPheSerCysAsnThrGlyTyrLysLeuPheGlySerThrSerSerPheCys
1323 ACCATCTCCTTCTCATGTAACACAGGGTACAAATTATTTGGCTCGACTTCTAGTTTTTGT

LeuIleSerGlySerSerValGlnTrpSerAspProLeuProGluCysArgGluIleTyr
         A   AAGC    TCGAG
1383 CTtATttcaGGCagctcTGTCCAGTGGAGTGACCCGTTGCCAGAGTGCAGAGAAATTTAT
         Acceptor 2

CysProAlaProProGlnIleAspAsnGlyIleIleGlnGlyGluArgAspHisTyrGly
1443 TGTCCAGCACCACCACAAATTGACAATGGAATAATTCAAGGGGAACGTGACCATTATGGA

TyrArgGlnSerValThrTyrAlaCysAsnLysGlyPheThrMetIleGlyGluHisSer
1503 TATAGACAGTCTGTAACGTATGCATGTAATAAAGGATTCACCATGATTGGAGAGCACTCT
```

FIG. 1B

```
         IleTyrCysThrValAsnAsnAspGluGlyGluTrpSerGlyProProProGluCysArg
1563 ATTTATTGTACTGTGAATAATGATGAAGGAGAGTGGAGTGGCCCACCACCTGAATGCAGA

GlyLysSerLeuThrSerLysValProProThrValGlnLysProThrThrValAsnVal
1623 GGAAAATCTCTAACTTCCAAGGTCCCACCAACAGTTCAGAAACCTACCACAGTAAATGTT

ProThrThrGluValSerProThrSerGlnLysThrThrThrLysThrThrThrProAsn
1683 CCAACTACAGAAGTCTCACCAACTTCTCAGAAAACCACCACAAAAACCACCACACCAAAT

AlaGlnAlaThrArgSerThrProValSerArgThrThrLysHisPheHisGluThrThr
1743 GCTCAAGCAACACGGAGTACACCTGTTTCCAGGACAACCAAGCATTTTCATGAAACAACC

ProAsnLysGlySerGlyThrThrSerGlyThrThrArgOP
1803 CCAAATAAAGGAAGTGGAACCACTTCAGGTACTACCCGTTGATCTAGA
```

FIG. IC

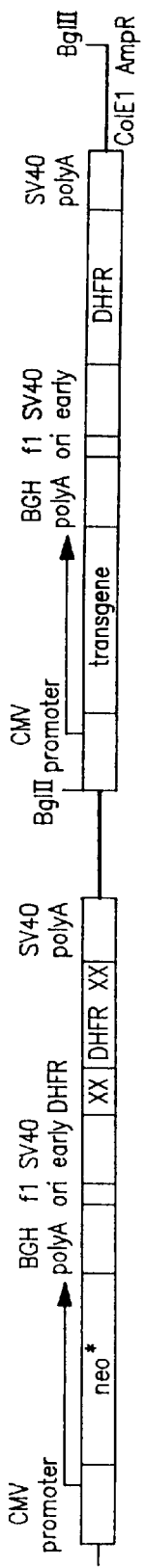
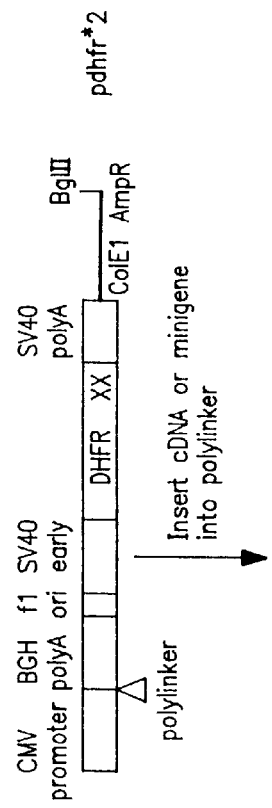
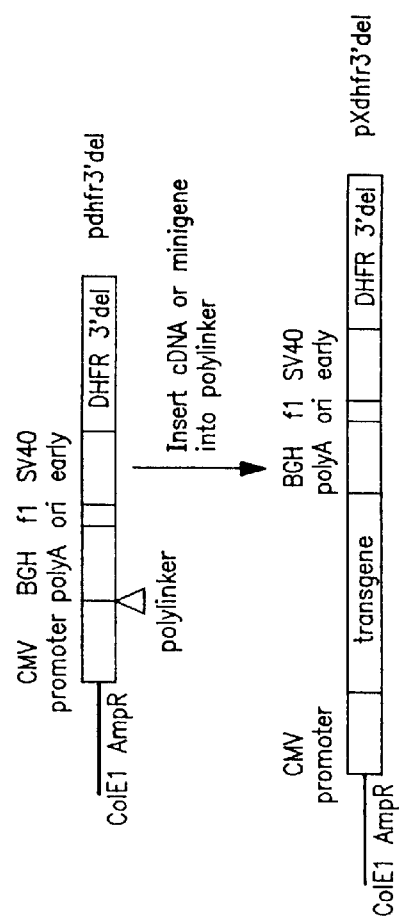
FIG. 7
FIG. 8
FIG. 9

SEQUENCE LISTING

<160> NUMBER OF SEQ ID NOS: 33

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: primer D182E (M1) #1

<400> SEQUENCE: 1
gggtcacgac gagatcatcg ccgt                                            24

```
<210> SEQ ID NO 2
<211> LENGTH: 23
<212> TYPE: DNA
<213> ORGANISM: Artificial Sequence
<220> FEATURE:
<223> OTHER INFORMATION: Description of Artificial  Sequence: primer D182
      (M1) #2

<400> SEQUENCE: 2
tctagtagcg gcagcccgta cgc                                             23

<210> SEQ ID NO 3
<211> LENGTH: 26
<212> TYPE: DNA
<213> ORGANISM: Artificial Sequence
<220> FEATURE:
<223> OTHER INFORMATION: Description of Artificial  Sequence: primer
      D261N (M2) #1

<400> SEQUENCE: 3
tcccgctcag aagaactcgt taagaa                                          26

<210> SEQ ID NO 4
<211> LENGTH: 22
<212> TYPE: DNA
<213> ORGANISM: Artificial Sequence
<220> FEATURE:
<223> OTHER INFORMATION: Description of Artificial  Sequence: primer
      D261N (M2) #2

<400> SEQUENCE: 4
tcttgagcaa tcttccgcta tc                                              22

<210> SEQ ID NO 5
<211> LENGTH: 44
<212> TYPE: DNA
<213> ORGANISM: Artificial Sequence
<220> FEATURE:
<223> OTHER INFORMATION: Description of Artificial  Sequence: dhfr primer
      #5

<400> SEQUENCE: 5
cgtagcagcg gcacagggtt attatcccct aaccgttctt gctc                      44

<210> SEQ ID NO 6
<211> LENGTH: 27
<212> TYPE: DNA
<213> ORGANISM: Artificial Sequence
<220> FEATURE:
<223> OTHER INFORMATION: Description of Artificial  Sequence: dhfr primer
      #6

<400> SEQUENCE: 6
agggaggctt ttttggaggc ctaggct                                         27

<210> SEQ ID NO 7
<211> LENGTH: 45
<212> TYPE: DNA
<213> ORGANISM: Artificial Sequence
<220> FEATURE:
<223> OTHER INFORMATION: Description of Artificial  Sequence: dhfr primer
      #7

<400> SEQUENCE: 7
gcatcgtcgc cgtgtcccaa taatagggga ttggcaagaa cggag                     45
```

```
<210> SEQ ID NO 8
<211> LENGTH: 35
<212> TYPE: DNA
<213> ORGANISM: Artificial Sequence
<220> FEATURE:
<223> OTHER INFORMATION: Description of Artificial  Sequence: dhfr primer
      #8

<400> SEQUENCE: 8
gagacgaggg gaggatttcg atacgaagct tacgg                                 35

<210> SEQ ID NO 9
<211> LENGTH: 46
<212> TYPE: DNA
<213> ORGANISM: Artificial Sequence
<220> FEATURE:
<223> OTHER INFORMATION: Description of Artificial  Sequence: dhfr primer
      #9

<400> SEQUENCE: 9
cccctttata tttgaagagg gtattatcgg tccgcaggag agactc                     46

<210> SEQ ID NO 10
<211> LENGTH: 46
<212> TYPE: DNA
<213> ORGANISM: Artificial Sequence
<220> FEATURE:
<223> OTHER INFORMATION: Description of Artificial  Sequence: dhfr primer
      #10

<400> SEQUENCE: 10
ggggaaatat aaacttctcc cataatagcc aggcgtcctc tctgag                     46

<210> SEQ ID NO 11
<211> LENGTH: 33
<212> TYPE: DNA
<213> ORGANISM: Artificial Sequence
<220> FEATURE:
<223> OTHER INFORMATION: Description of Artificial  Sequence: CAB2H3-1

<400> SEQUENCE: 11
cagaaagctt tcttcacatt tgtacgttat tac                                   33

<210> SEQ ID NO 12
<211> LENGTH: 35
<212> TYPE: DNA
<213> ORGANISM: Artificial Sequence
<220> FEATURE:
<223> OTHER INFORMATION: Description of Artificial  Sequence: DAFTH5-1

<400> SEQUENCE: 12
cagaaagctt tgtgaaaatt cctggcgaga aggac                                 35

<210> SEQ ID NO 13
<211> LENGTH: 4
<212> TYPE: PRT
<213> ORGANISM: CAB-2

<400> SEQUENCE: 13

Gly Lys Pro Pro
  1

<210> SEQ ID NO 14
<211> LENGTH: 3
<212> TYPE: PRT
<213> ORGANISM: CAB-2
```

```
<210> SEQ ID NO 14

Tyr Phe Pro
 1

<210> SEQ ID NO 15
<211> LENGTH: 15
<212> TYPE: DNA
<213> ORGANISM: Artificial Sequence
<220> FEATURE:
<223> OTHER INFORMATION: Description of Artificial  Sequence: modified
      acceptor site 1

<400> SEQUENCE: 15
cttatttcaa gctct                                                          15

<210> SEQ ID NO 16
<211> LENGTH: 6
<212> TYPE: PRT
<213> ORGANISM: CAB-2

<400> SEQUENCE: 16

Leu Ile Ser Gly Ser Ser
 1               5

<210> SEQ ID NO 17
<211> LENGTH: 15
<212> TYPE: DNA
<213> ORGANISM: Artificial Sequence
<220> FEATURE:
<223> OTHER INFORMATION: Description of Artificial  Sequence: modified
      acceptor site 2

<400> SEQUENCE: 17
ctaataagct cgagt                                                          15

<210> SEQ ID NO 18
<211> LENGTH: 25
<212> TYPE: DNA
<213> ORGANISM: Artificial Sequence
<220> FEATURE:
<223> OTHER INFORMATION: Description of Artificial  Sequence: primer
      SACOL5P

<400> SEQUENCE: 18
tatggagctc atcgggaaac caaaa                                               25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial  Sequence: primer
      SACOL3P

<400> SEQUENCE: 19
ctcgagtagc cctttggttt tggg                                                24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial  Sequence: primer
      NDE3P

<400> SEQUENCE: 20
```

```
tcgccttttg gggggtatac actt                                          24
```

<210> SEQ ID NO 21
<211> LENGTH: 24
<212> TYPE: DNA
<213> ORGANISM: Artificial Sequence
<220> FEATURE:
<223> OTHER INFORMATION: Description of Artificial  Sequence: primer
     NDE5P

<400> SEQUENCE: 21

```
agcggaaaac cccccatatg tgaa                                          24
```

<210> SEQ ID NO 22
<211> LENGTH: 27
<212> TYPE: DNA
<213> ORGANISM: Artificial Sequence
<220> FEATURE:
<223> OTHER INFORMATION: Description of Artificial  Sequence: primer
     ACCOL5P

<400> SEQUENCE: 22

```
atcactcaga attacttccc tgtcggt                                       27
```

<210> SEQ ID NO 23
<211> LENGTH: 27
<212> TYPE: DNA
<213> ORGANISM: Artificial Sequence
<220> FEATURE:
<223> OTHER INFORMATION: Description of Artificial  Sequence: primer
     ACCOL3P

<400> SEQUENCE: 23

```
gtcttaatga agggacagcc atgacaa                                       27
```

<210> SEQ ID NO 24
<211> LENGTH: 25
<212> TYPE: DNA
<213> ORGANISM: Artificial Sequence
<220> FEATURE:
<223> OTHER INFORMATION: Description of Artificial  Sequence: primer
     ACCXH05P

<400> SEQUENCE: 24

```
aataagcggc tcgagtgtcc agtgg                                         25
```

<210> SEQ ID NO 25
<211> LENGTH: 27
<212> TYPE: DNA
<213> ORGANISM: Artificial Sequence
<220> FEATURE:
<223> OTHER INFORMATION: Description of Artificial  Sequence: primer
     ACCXH03P

<400> SEQUENCE: 25

```
aaaacagatt attcgccgag ctcacag                                       27
```

<210> SEQ ID NO 26
<211> LENGTH: 34
<212> TYPE: DNA
<213> ORGANISM: Artificial Sequence
<220> FEATURE:
<223> OTHER INFORMATION: Description of Artificial  Sequence: primer
     MCPK5-2

<400> SEQUENCE: 26

```
cagaggtacc atggagcctc ccggccgccg cgag                               34
```

-continued

```
<210> SEQ ID NO 27
<211> LENGTH: 39
<212> TYPE: DNA
<213> ORGANISM: Artificial Sequence
<220> FEATURE:
<223> OTHER INFORMATION: Description of Artificial  Sequence: primer
      DAFSXB32

<400> SEQUENCE: 27
cttggtgaag tccatgatgg gcaactatta gatctaaac                        39

<210> SEQ ID NO 28
<211> LENGTH: 31
<212> TYPE: DNA
<213> ORGANISM: Artificial Sequence
<220> FEATURE:
<223> OTHER INFORMATION: Description of Artificial  Sequence: primer
      STTDELE3

<400> SEQUENCE: 28
cagagaattc tcatgttggt gggaccttgg a                                31

<210> SEQ ID NO 29
<211> LENGTH: 33
<212> TYPE: DNA
<213> ORGANISM: Artificial Sequence
<220> FEATURE:
<223> OTHER INFORMATION: Description of Artificial  Sequence: primer
      STDELE31

<400> SEQUENCE: 29
cagagaattc tcattttcct ctgcattcag gac                              33

<210> SEQ ID NO 30
<211> LENGTH: 106
<212> TYPE: DNA
<213> ORGANISM: Artificial Sequence
<220> FEATURE:
<223> OTHER INFORMATION: Description of Artificial  Sequence: primer
      CAB4-33P

<400> SEQUENCE: 30
cagagaattc tcacatattt ttaacaaaaa tttcttcata tgctattttc a ctctctgct    60 tctttctttt tcttttggtt ttttttcctc tgcattcagg tggtgg                  106

<210> SEQ ID NO 31
<211> LENGTH: 1848
<212> TYPE: DNA
<213> ORGANISM: CAB2
<220> FEATURE:
<221> NAME/KEY: CDS
<222> LOCATION: (7)..(1839)

<400> SEQUENCE: 31 ggccgc atg gag cct ccc ggc cgc cgc gag tgt ccc ttt cct tcc tgg       48
       Met Glu Pro Pro Gly Arg A rg Glu Cys Pro Phe Pro Ser Trp
        1               5                   10 cgc ttt cct ggg ttg ctt ctg gcg gcc atg g tg ttg ctg ctg tac tcc    96
Arg Phe Pro Gly Leu Leu Leu Ala Ala Met V al Leu Leu Leu Tyr Ser
 15                  20                  25                  30 ttc tcc gat gcc tgt gag gag cca cca aca t tt gaa gct atg gag ctc   144
Phe Ser Asp Ala Cys Glu Glu Pro Pro Thr P he Glu Ala Met Glu Leu
                35                  40                  45 att ggt aaa cca aaa ccc tac tat gag att g gt gaa cga gta gat tat   192
```

```
Ile Gly Lys Pro Lys Pro Tyr Tyr Glu Ile Gly Glu Arg Val Asp Tyr
            50                  55                  60 aag tgt aaa aaa gga tac ttc tat ata cct c ct ctt gcc acc cat act       240
Lys Cys Lys Lys Gly Tyr Phe Tyr Ile Pro P ro Leu Ala Thr His Thr
        65                  70                  75 att tgt gat cgg aat cat aca tgg cta cct g tc tca gat gac gcc tgt       288
Ile Cys Asp Arg Asn His Thr Trp Leu Pro V al Ser Asp Asp Ala Cys
    80                  85                      90 tat aga gaa aca tgt cca tat ata cgg gat c ct tta aat ggc caa gca       336
Tyr Arg Glu Thr Cys Pro Tyr Ile Arg Asp P ro Leu Asn Gly Gln Ala
95                  100                 105                 110 gtc cct gca aat ggg act tac gag ttt ggt t at cag atg cac ttt att       384
Val Pro Ala Asn Gly Thr Tyr Glu Phe Gly T yr Gln Met His Phe Ile
            115                 120                 125 tgt aat gag ggt tat tac tta att ggt gaa g aa att cta tat tgt gaa       432
Cys Asn Glu Gly Tyr Tyr Leu Ile Gly Glu G lu Ile Leu Tyr Cys Glu
        130                 135                 140 ctt aaa gga tca gta gca att tgg agc ggt a ag ccc cca ata tgt gaa       480
Leu Lys Gly Ser Val Ala Ile Trp Ser Gly L ys Pro Pro Ile Cys Glu
    145                 150                 155 aag gtt ttg tgt aca cca cct cca aaa ata a aa aat gga aaa cac acc       528
Lys Val Leu Cys Thr Pro Pro Pro Lys Ile L ys Asn Gly Lys His Thr
160                 165                 170 ttt agt gaa gta gaa gta ttt gag tat ctt g at gca gta act tat agt       576
Phe Ser Glu Val Glu Val Phe Glu Tyr Leu A sp Ala Val Thr Tyr Ser
175                 180                 185                 190 tgt gat cct gca cct gga cca gat cca ttt t ca ctt att gga gag agc       624
Cys Asp Pro Ala Pro Gly Pro Asp Pro Phe S er Leu Ile Gly Glu Ser
            195                 200                 205 acg att tat tgt ggt gac aat tca gtg tgg a gt cgt gct gct cca gag       672
Thr Ile Tyr Cys Gly Asp Asn Ser Val Trp S er Arg Ala Ala Pro Glu
        210                 215                 220 tgt aaa gtg gtc aaa tgt cga ttt cca gta g tc gaa aat gga aaa cag       720
Cys Lys Val Val Lys Cys Arg Phe Pro Val V al Glu Asn Gly Lys Gln
    225                 230                 235 ata tca gga ttt gga aaa aaa ttt tac tac a aa gca aca gtt atg ttt       768
Ile Ser Gly Phe Gly Lys Lys Phe Tyr Tyr L ys Ala Thr Val Met Phe
240                 245                 250 gaa tgc gat aag ggt ttt tac ctc gat ggc a gc gac aca att gtc tgt       816
Glu Cys Asp Lys Gly Phe Tyr Leu Asp Gly S er Asp Thr Ile Val Cys
255                 260                 265                 270 gac agt aac agt act tgg gat ccc cca gtt c ca aag tgt ctt aaa gtg       864
Asp Ser Asn Ser Thr Trp Asp Pro Pro Val P ro Lys Cys Leu Lys Val
            275                 280                 285 tcg act gac tgt ggc ctt ccc cca gat gta c ct aat gcc cag cca gct       912
Ser Thr Asp Cys Gly Leu Pro Pro Asp Val P ro Asn Ala Gln Pro Ala
        290                 295                 300 ttg gaa ggc cgt aca agt ttt ccc gag gat a ct gta ata acg tac aaa       960
Leu Glu Gly Arg Thr Ser Phe Pro Glu Asp T hr Val Ile Thr Tyr Lys
    305                 310                 315 tgt gaa gaa agc ttt gtg aaa att cct ggc g ag aag gac tca gtg atc       1008
Cys Glu Glu Ser Phe Val Lys Ile Pro Gly G lu Lys Asp Ser Val Ile
320                 325                 330 tgc ctt aag ggc agt caa tgg tca gat att g aa gag ttc tgc aat cgt       1056
Cys Leu Lys Gly Ser Gln Trp Ser Asp Ile G lu Glu Phe Cys Asn Arg
335                 340                 345                 350 agc tgc gag gtg cca aca agg cta aat tct g ca tcc ctc aaa cag cct       1104
Ser Cys Glu Val Pro Thr Arg Leu Asn Ser A la Ser Leu Lys Gln Pro
            355                 360                 365
```

-continued

```
tat atc act cag aat tat ttt cca gtc ggt a ct gtt gtg gaa tat gag    1152
Tyr Ile Thr Gln Asn Tyr Phe Pro Val Gly T hr Val Val Glu Tyr Glu
        370                 375                 380 tgc cgt cca ggt tac aga aga gaa cct tct c ta tca cca aaa cta act    1200
Cys Arg Pro Gly Tyr Arg Arg Glu Pro Ser L eu Ser Pro Lys Leu Thr
        385                 390                 395 tgc ctt cag aat tta aaa tgg tcc aca gca g tc gaa ttt tgt aaa aag    1248
Cys Leu Gln Asn Leu Lys Trp Ser Thr Ala V al Glu Phe Cys Lys Lys
    400                 405                 410 aaa tca tgc cct aat ccg gga gaa ata cga a at ggt cag att gat gta    1296
Lys Ser Cys Pro Asn Pro Gly Glu Ile Arg A sn Gly Gln Ile Asp Val
415                 420                 425                 430 cca ggt ggc ata tta ttt ggt gca acc atc t cc ttc tca tgt aac aca    1344
Pro Gly Gly Ile Leu Phe Gly Ala Thr Ile S er Phe Ser Cys Asn Thr
                435                 440                 445 ggg tac aaa tta ttt ggc tcg act tct agt t tt tgt ctt att tca ggc    1392
Gly Tyr Lys Leu Phe Gly Ser Thr Ser Ser P he Cys Leu Ile Ser Gly
        450                 455                 460 agc tct gtc cag tgg agt gac ccg ttg cca g ag tgc aga gaa att tat    1440
Ser Ser Val Gln Trp Ser Asp Pro Leu Pro G lu Cys Arg Glu Ile Tyr
        465                 470                 475 tgt cca gca cca cca caa att gac aat gga a ta att caa ggg gaa cgt    1488
Cys Pro Ala Pro Pro Gln Ile Asp Asn Gly I le Ile Gln Gly Glu Arg
    480                 485                 490 gac cat tat gga tat aga cag tct gta acg t at gca tgt aat aaa gga    1536
Asp His Tyr Gly Tyr Arg Gln Ser Val Thr T yr Ala Cys Asn Lys Gly
495                 500                 505                 510 ttc acc atg att gga gag cac tct att tat t gt act gtg aat aat gat    1584
Phe Thr Met Ile Gly Glu His Ser Ile Tyr C ys Thr Val Asn Asn Asp
                515                 520                 525 gaa gga gag tgg agt ggc cca cca cct gaa t gc aga gga aaa tct cta    1632
Glu Gly Glu Trp Ser Gly Pro Pro Pro Glu C ys Arg Gly Lys Ser Leu
        530                 535                 540 act tcc aag gtc cca cca aca gtt cag aaa c ct acc aca gta aat gtt    1680
Thr Ser Lys Val Pro Pro Thr Val Gln Lys P ro Thr Thr Val Asn Val
        545                 550                 555 cca act aca gaa gtc tca cca act tct cag a aa acc acc aca aaa acc    1728
Pro Thr Thr Glu Val Ser Pro Thr Ser Gln L ys Thr Thr Thr Lys Thr
    560                 565                 570 acc aca cca aat gct caa gca aca cgg agt a ca cct gtt tcc agg aca    1776
Thr Thr Pro Asn Ala Gln Ala Thr Arg Ser T hr Pro Val Ser Arg Thr
575                 580                 585                 590 acc aag cat ttt cat gaa aca acc cca aat a aa gga agt gga acc act    1824
Thr Lys His Phe His Glu Thr Thr Pro Asn L ys Gly Ser Gly Thr Thr
                595                 600                 605 tca ggt act acc cgt tgatctaga                                       1848
Ser Gly Thr Thr Arg
        610

<210> SEQ ID NO 32
<211> LENGTH: 611
<212> TYPE: PRT
<213> ORGANISM: CAB2

<400> SEQUENCE: 32

Met Glu Pro Pro Gly Arg Arg Glu Cys Pro P he Pro Ser Trp Arg Phe
 1               5                  10                  15

Pro Gly Leu Leu Leu Ala Ala Met Val Leu L eu Leu Tyr Ser Phe Ser
                20                  25                  30

Asp Ala Cys Glu Glu Pro Pro Thr Phe Glu A la Met Glu Leu Ile Gly
```

-continued

```
                    35                  40                  45
Lys Pro Lys Pro Tyr Tyr Glu Ile Gly Glu A rg Val Asp Tyr Lys Cys
            50                  55                  60
Lys Lys Gly Tyr Phe Tyr Ile Pro Pro Leu A la Thr His Thr Ile Cys
 65                  70                  75                  80
Asp Arg Asn His Thr Trp Leu Pro Val Ser A sp Asp Ala Cys Tyr Arg
                85                  90                  95
Glu Thr Cys Pro Tyr Ile Arg Asp Pro Leu A sn Gly Gln Ala Val Pro
                100                 105                 110
Ala Asn Gly Thr Tyr Glu Phe Gly Tyr Gln M et His Phe Ile Cys Asn
                115                 120                 125
Glu Gly Tyr Tyr Leu Ile Gly Glu Ile L eu Tyr Cys Glu Leu Lys
                130                 135                 140
Gly Ser Val Ala Ile Trp Ser Gly Lys Pro P ro Ile Cys Glu Lys Val
145                 150                 155                 160
Leu Cys Thr Pro Pro Lys Ile Lys Asn G ly Lys His Thr Phe Ser
                165                 170                 175
Glu Val Glu Val Phe Glu Tyr Leu Asp Ala V al Thr Tyr Ser Cys Asp
                180                 185                 190
Pro Ala Pro Gly Pro Asp Pro Phe Ser Leu I le Gly Glu Ser Thr Ile
                195                 200                 205
Tyr Cys Gly Asp Asn Ser Val Trp Ser Arg A la Ala Pro Glu Cys Lys
                210                 215                 220
Val Val Lys Cys Arg Phe Pro Val Val Glu A sn Gly Lys Gln Ile Ser
225                 230                 235                 240
Gly Phe Gly Lys Lys Phe Tyr Tyr Lys Ala T hr Val Met Phe Glu Cys
                245                 250                 255
Asp Lys Gly Phe Tyr Leu Asp Gly Ser Asp T hr Ile Val Cys Asp Ser
                260                 265                 270
Asn Ser Thr Trp Asp Pro Pro Val Pro Lys C ys Leu Lys Val Ser Thr
                275                 280                 285
Asp Cys Gly Leu Pro Pro Asp Val Pro Asn A la Gln Pro Ala Leu Glu
                290                 295                 300
Gly Arg Thr Ser Phe Pro Glu Asp Thr Val I le Thr Tyr Lys Cys Glu
305                 310                 315                 320
Glu Ser Phe Val Lys Ile Pro Gly Glu Lys A sp Ser Val Ile Cys Leu
                325                 330                 335
Lys Gly Ser Gln Trp Ser Asp Ile Glu Glu P he Cys Asn Arg Ser Cys
                340                 345                 350
Glu Val Pro Thr Arg Leu Asn Ser Ala Ser L eu Lys Gln Pro Tyr Ile
                355                 360                 365
Thr Gln Asn Tyr Phe Pro Val Gly Thr Val V al Glu Tyr Glu Cys Arg
                370                 375                 380
Pro Gly Tyr Arg Arg Glu Pro Ser Leu Ser P ro Lys Leu Thr Cys Leu
385                 390                 395                 400
Gln Asn Leu Lys Trp Ser Thr Ala Val Glu P he Cys Lys Lys Lys Ser
                405                 410                 415
Cys Pro Asn Pro Gly Glu Ile Arg Asn Gly G ln Ile Asp Val Pro Gly
                420                 425                 430
Gly Ile Leu Phe Gly Ala Thr Ile Ser Phe S er Cys Asn Thr Gly Tyr
                435                 440                 445
Lys Leu Phe Gly Ser Thr Ser Ser Phe Cys L eu Ile Ser Gly Ser Ser
                450                 455                 460
```

```
Val Gln Trp Ser Asp Pro Leu Pro Glu Cys A rg Glu Ile Tyr Cys Pro
465                 470                 475                 480

Ala Pro Pro Gln Ile Asp Asn Gly Ile Ile G ln Gly Glu Arg Asp His
                485                 490                 495

Tyr Gly Tyr Arg Gln Ser Val Thr Tyr Ala C ys Asn Lys Gly Phe Thr
                500                 505                 510

Met Ile Gly Glu His Ser Ile Tyr Cys Thr V al Asn Asn Asp Glu Gly
            515                 520                 525

Glu Trp Ser Gly Pro Pro Glu Cys Arg G ly Lys Ser Leu Thr Ser
        530                 535                 540

Lys Val Pro Pro Thr Val Gln Lys Pro Thr T hr Val Asn Val Pro Thr
545                 550                 555                 560

Thr Glu Val Ser Pro Thr Ser Gln Lys Thr T hr Thr Lys Thr Thr Thr
                565                 570                 575

Pro Asn Ala Gln Ala Thr Arg Ser Thr Pro V al Ser Arg Thr Thr Lys
                580                 585                 590

His Phe His Glu Thr Thr Pro Asn Lys Gly S er Gly Thr Thr Ser Gly
            595                 600                 605

Thr Thr Arg
    610

<210> SEQ ID NO 33
<211> LENGTH: 4
<212> TYPE: PRT
<213> ORGANISM: Artificial Sequence
<220> FEATURE:
<223> OTHER INFORMATION: Description of Artificial  Sequence: spacer

<400> SEQUENCE: 33

Gly Gly Gly Ser
 1
```

EXPRESSION VECTORS, TRANSFECTION SYSTEMS, AND METHOD OF USE THEREOF

CROSS-REFERENCE TO RELATED APPLICATION

This application is a divisional of U.S. patent application Ser. No. 09/475,460, filed Dec. 30, 1999, now U.S. Pat. No. 6,316,253 on Nov. 13, 2001 from which application priority is claimed pursuant to 35 U.S.C. §120, and this application is related to Provisional Patent Application Ser. No. 60/162,930, filed Nov. 1, 1999, from which priority is claimed under 35 USC §119(e)(1), and which applications are incorporated herein by reference in their entireties.

FIELD OF THE INVENTION

The invention provides novel expression vectors that allow stable, high-level expression of a polypeptide of interest in a host cell, particularly mammalian cells. The invention also includes a transfection system for mammalian cells using the constructs described herein. The invention described herein provides an efficient mechanism by which any desired polypeptide can be expressed at high levels using novel cell lines generated as described herein.

BACKGROUND OF THE IVVENTION

Vectors based on lytic viruses such as polyoma have been used for short-term expression, but tend to be unstable, and replicate many times per cell cycle (Lebkowski, J. S., et al., MOL. CELL. BIOL. 4:1951–1960, 1984). Vectors based on bovine papilloma virus have also been developed but do not consistently replicate once per cell cycle (Gilbert, D. M., et al., CELL 50:59–68, 1987; Ravnan, J.-B., et al., J. VIROL. 66:6946–6952, 1992). Further bovine papilloma virus-based vectors show a high frequency of rearrangements (Ashman, C. R., et al., SOMATIC CELL MOL. GENET. 11:499–504, 1985; DuBridge, R. B., et al., MOL. CELL. BIOL. 7:379–387, 1987).

In human and primate cells, vectors based on Epstein-Barr virus (EBV) have been developed (Yates, J., et al., PROC. NATL. ACAD. Sci. USA. 81:3806–3810, 1984; Reisman, D., et al., MOL. CELL. BIOL. 5:1822–1832, 1985; Lupton, S., et al., MOL. CELL. BIOL. 5:2533–2542, 1985). These vectors typically replicate once per cell cycle (Adams, A., J. VIROL. 61:1743–1746, 1987; Yates, J. L., et al., J. VIROLOGY 65:483–488, 1991; Haase, S. B., et al., NUC. ACIDS RES. 19:5053–5058, 1991) and are stably maintained over the long-term with a low mutation frequency (DuBridge, R. B., et al., MOL. CELL. BIOL. 7:379–387, 1987; DuBridge, R. B., et al., MUTAGENESIS 3:1–9, 1988; Drinkwater, N. R., et al., PROC. NATL. ACAD. SCI. USA 83: 3402–3406, 1986). These vectors have been used for cloning and expression studies in human and simian cells (Margolskee, R. F., et al., MOL. CELL. BIOL. 8:2837–2847, 1988; Young, J. M., et al., GENE 62:171–185, 1988; Belt, P.B.G.M., et al., GENE 84:407–417, 1989; Peterson, C., et al., GENE 107:279–284, 1991). Stable transformation frequencies are high because integration into the genome is not required, and recovery of cloned sequences is achieved by plasmid extraction. However, rodent cells are not permissive for EBV replication, and no rodent counterpart of EBV has been described (Yates, J. L., et al., NATURE (LONDON) 313:812–815, 1985).

U.S. Pat. No. 4,959,317 (Sauer, et al.) discloses the use of Cre-Lox site-specific recombination to achieve gene transfer in eukaryotic cells. However, the system described does not provide efficient or stable integration of transferred DNA into the host genome (see e.g., (Sauer, et al., (1993) Methods in Enzymology 225: page 898). This is largely due to the fact that excision of transferred DNA out of the genome, by way of intramolecular exchange, predominates over integration of DNA into the genome, by way of intermolecular site-specific recombination.

U.S. Pat. No. 5,928,914 (Leboulch, et al.) describes methods and compositions for transforming cells, resulting in efficient and stable site-specific integration of transgenes. Transformation is achieved by introducing into a cell an acceptor vector, preferably a retroviral vector, which integrates into the genome of the cell. The acceptor vector comprises two incompatible lox sequences, L1 and L2. A donor vector is then introduced into the cell comprising a transgene flanked by the same L1 and L2 sequences. Stable gene transfer is initiated by contacting the lox L1 and L2 sequences with Cre recombinase.

SUMMARY OF THE INVENTION

In one aspect, the invention provides an expression vector comprising (a) a first polynucleotide encoding a first, crippled, selectable marker (b) a second polynucleotide encoding a heterologous polypeptide of interest; and (c) a third polynucleotide encoding a second, amplifiable selectable marker. Suitable first selectable markers include sequences coding antibiotic (e.g., neomycin) resistance containing one or more crippling mutations. In one embodiment, the amplifiable selectable marker is dihydrofolate reducatase (dhfr).

The invention also includes the following constructs: a plasmid designated pESN1dhfr; a plasmid designated pESN2dhfr; plasmid designated pESN3dhfr; a plasmid designated pneo*dhfr5'del (e.g., pneo1dhfr5'del, pneo2dhfr5'del, pneo3dhfr5'del); and a plasmid designated pdhfr3'del.

In another aspect the invention includes a method for producing a polypeptide of interest in a host cell, comprising (a) introducing an expression vector or construct described herein into a host cell, (b) selecting host cells which express the first and second selectable markers under conditions that select for stably integrated expression vectors, (c) growing the stably-transfected host cells under conditions which favor expression of the polypeptide of interest, and (d) isolating the polypeptide of interest.

In certain embodiments, the heterologous polypeptide is a viral protein (e.g., an HIV protein) or is CAB2 or CAB4 and the host cell is a mammalian or insect cell. Host cell lines that produces a polypeptide of interest using this method are also included in the present invention.

In another aspect, the invention includes a transfection system comprising (a) a first construct comprising, in a suitable backbone, a sequence encoding a first selectable marker and a sequence encoding a second selectable marker, wherein the second selectable marker contains at least one disabling mutation in its coding sequence; and (b) a second construct comprising, in a suitable backbone, a polynucleotide sequence of interest and a sequence encoding a third selectable marker, wherein the third selectable marker is the same selectable marker as the second selectable marker except that the third selectable marker contains at least one disabling mutation that is in a different region of the coding sequence than the disabling mutation in said second selectable marker. In certain embodiments, the first selectable marker encodes for antibiotic resistance, for example, by encoding wild-type or functionally impaired neomycin phosphotransferase II, the second selectable marker encodes dhfr which disabled by at least one mutation in the 5' coding region and the third selectable marker encodes dhfr which is disabled by at least one different mutation in the 3' coding region. The disabling mutations may be, by way of example, point mutations or deletions. Where the constructs are plasmids, the transfection system may further comprise (c) first, second, and third promoters operably linked to said first and second selectable markers and said transgene, respectively;

(d) sequences encoding polyadenylation sites operably linked to said first and second selectable markers and said transgene; and (e) sequence encoding origins of replication operably linked to said first, second selectable markers and said transgene. Promoters such as CMV promoter, an RSV promoter or an SV-40 early promoter may be used and each sequence may be operably linked to a different promoter.

In another aspect, the invention includes a method for producing a mammalian cell line for expression of a selected polynucleotide sequence, comprising (a) introducing into a selected mammalian cell, having a genome, a first construct comprising a sequence encoding a first selectable marker and a sequence encoding a second selectable marker, wherein the second selectable marker contains at least one disabling mutation in its coding sequence, (b) selecting for a mammalian cell expressing the first selectable marker, wherein said first construct stably integrates into the genome;

(c) introducing into the mammalian cell a second construct comprising a polynucleotide sequence of interest and a sequence encoding a third selectable marker, wherein the third selectable marker is the same selectable marker as the second selectable marker except that the third selectable marker contains at least one disabling mutation that is in a different region of the coding sequence than the disabling mutation in said second selectable marker; and (d) selecting for a mammalian cell expressing a functional product encoded by the second selectable marker, wherein the functional product is encoded by a sequence produced by a recombination event between said second and third selectable markers, and the resulting mammalian cell is capable of expressing the selected polynucleotide sequence. In certain embodiments, the selected polynucleotide sequence encodes a polypeptide and expressing the selected polynucleotide sequence results in expression of the polypeptide. Mammalian cells produced by this method are also provided.

In another aspect, the invention includes a method for producing a polypeptide of interest in a host mammalian cell, said method comprising:

(a) introducing into said cell, having a genome, a first construct comprising a sequence encoding a first selectable marker and a sequence encoding a second selectable marker, wherein the selectable marker contains at least one disabling mutation in its coding sequence;

(b) selecting for a mammalian cell expressing the first selectable marker, wherein said first construct stably integrates into the genome;

(c) introducing into the mammalian cell a second construct comprising a polynucleotide sequence encoding the polypeptide of interest and a sequence encoding a third selectable marker, wherein the third selectable marker is the same selectable marker as the second selectable marker except that the third selectable marker contains at least one disabling mutation that is in a different region of the coding sequence than the disabling mutation in said second selectable marker;

(d) selecting for a mammalian cell expressing a functional product encoded by the second selectable marker, wherein the functional product is encoded by a sequence produced by a recombination event between said second and third selectable markers, and the resulting mammalian cell is capable of expressing the polypeptide of interest; and culturing the mammalian cell under conditions to produce the polypeptide of interest.

In one embodiment, the first selectable marker encodes for neomycin resistance and second and third selectable markers encode dhfr. In certain embodiments, the constructs can be introduced into said cells by electroporation or by calcium phosphate transfection. A mammalian cell line that produced according to these methods are also included.

These and other embodiments will be readily apparent to one skilled in the art in light of the teachings of this specification.

BRIEF DESCRIPTION OF THE DRAWINGS

This invention will be more fully described with reference to the drawings in which:

FIG. 1 depicts the nucleotide sequence of CAB2 (SEQ ID NO:31). Lower case represents original sequence.

FIG. 7 shows the product of homologous recombination in which the disabled DHFR gene has been rescued and the transgene is positioned in the high expression locus of a mammalian cell genome by insertion of the transgene proximate to the mutant neo* gene.

FIG. 8 depicts the pdhfr*2 DNA construct; a transgene, such as a recombinant protein gene, can be inserted into the polylinker of pdhfr*2 to create pXdhfr*2.

FIG. 9 depicts a selection scheme, wherein the DNA construct identified as pdhfr3'del employs a deletion mutant of a DHFR gene and insertion of a transgene in a polylinker forms the construct designated pXdhfr3'del (e.g., pdhfr3'del).

DETAILED DESCRIPTION

Figure 2:
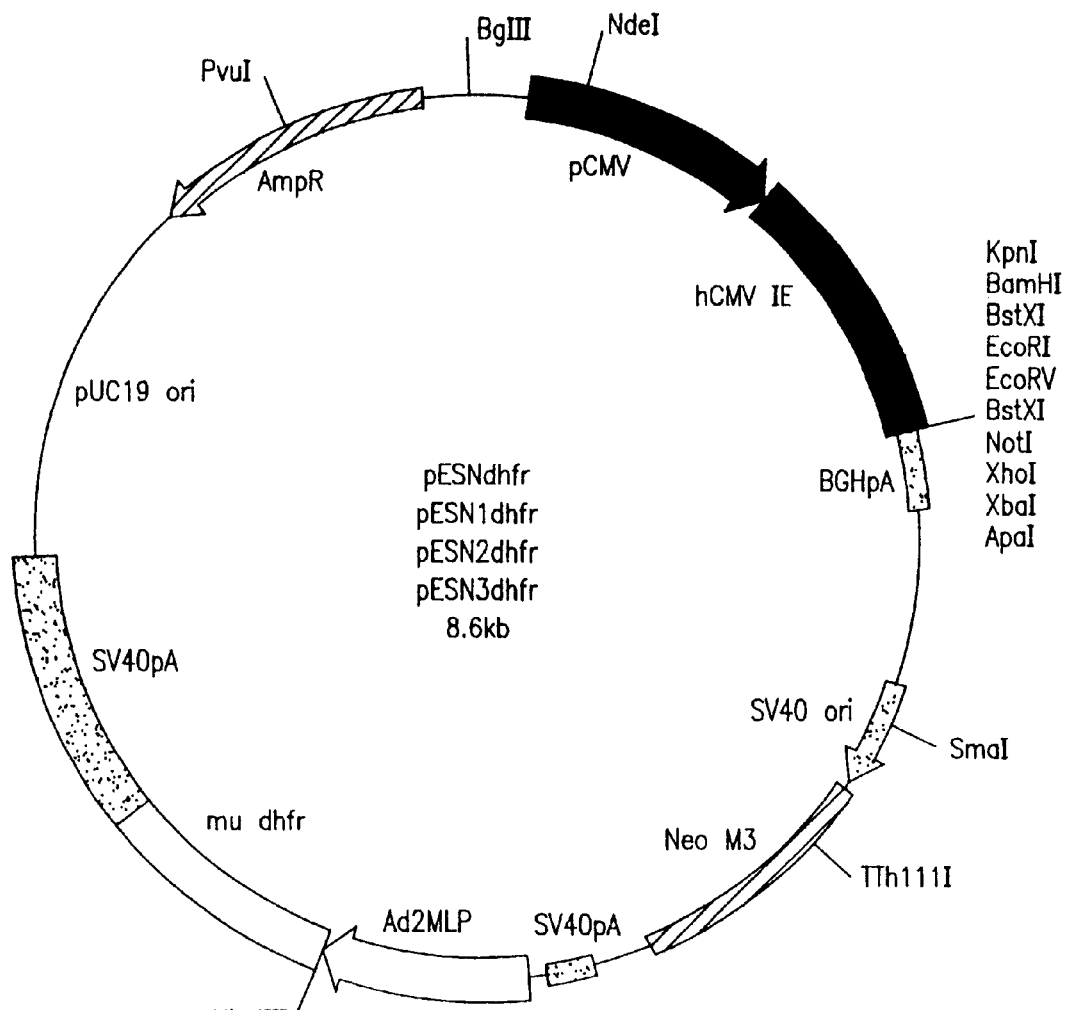
FIG. 2 is a schematic representation of expression vectors designated pESNdhfr, pESN1dhfr, pESN2dhfr and pESN3dhfr. The vectors differ in the location and/or number of mutations in the Neo gene. pESNdhfr contains a wild-type Neo sequence. pESN1dhfr contains a mutation which alters amino acid residue 182 of the Neo gene product. pESN2dhfr contains a mutation which alters amino acid residue 261 of the Neo gene product and pESN3dhfr contains mutations which alter both amino acid residues 182 and 261 of the Neo gene product.
Figure 3:
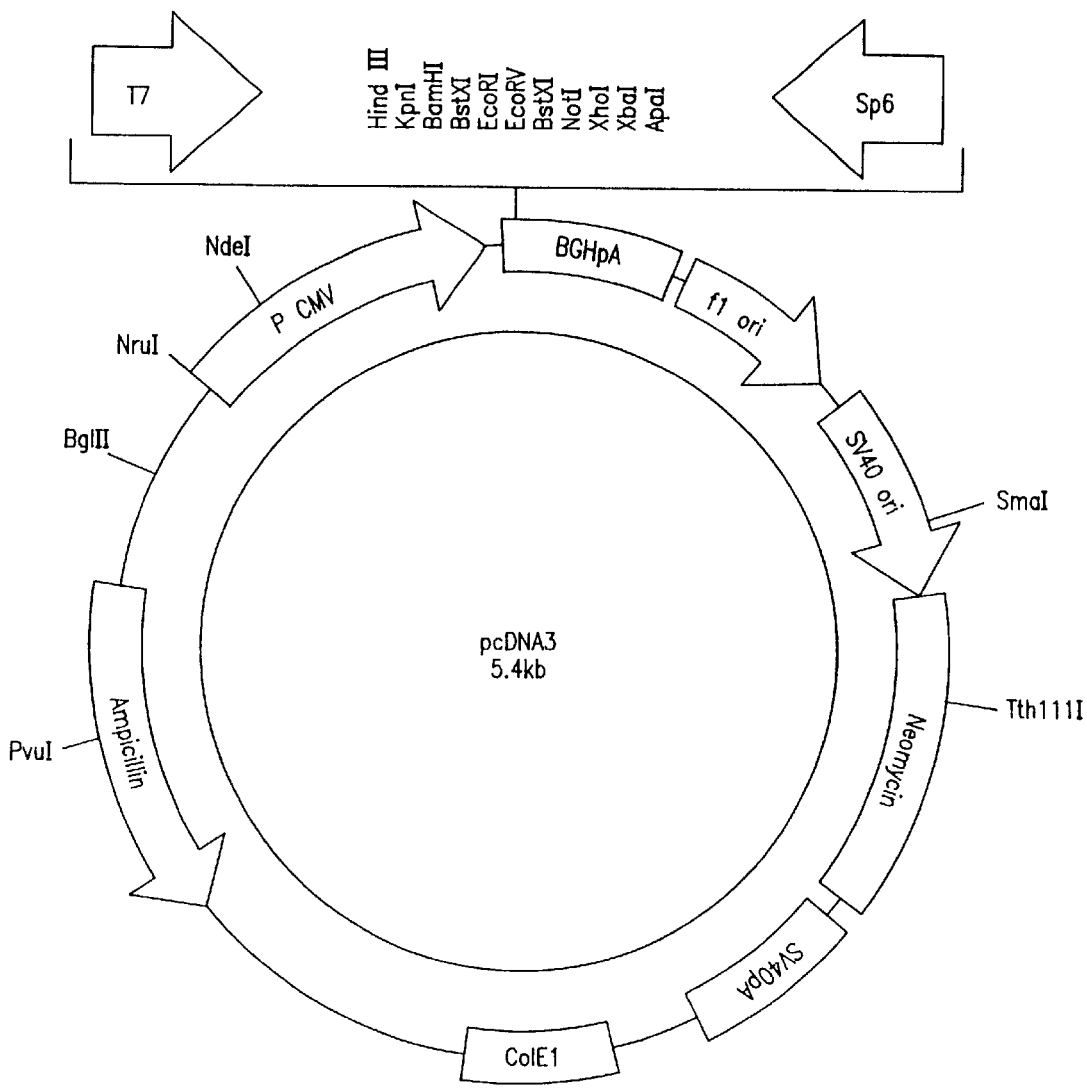
FIG. 3 is a schematic depicting an expression vector designated pcDNA3. The vector is 5446 nucleotides and contains, in a pUC19 vector backbone (bases 4450–5310), the following sequences: a CMV promoter (bases 209–863); a T7 promoter (bases 864–882); a polylinker (bases 889–994); a Sp6 promoter (bases 999–1016); a BGH polyA sequence (bases 1018–1249); and SV40 promoter (bases 1790–2215); an SV40 origin of replication (bases 19841–2069); an open reading frame (ORF) encoding neomycin resistance (Neo') (bases 2151–2932); an SV40 polyA sequence (bases 3120–3250); and an ORF encoding ampicillin resistance (Amp') (bases 4450–5310).

The invention provides novel expression vectors that allow stable, high-level expression of a polypeptide of interest in a host cell, particularly mammalian cells. The constructs comprise (i) a first sequence encoding a first selectable marker; (ii) a second sequence encoding a polypeptide product of interest (e.g. "transgene"); (iii) a third sequence encoding a second selectable marker. Typically, the three sequences are operably linked to at least one strong promoter, for example a CMV promoter to increase expression and promote correct splicing of the product of interest.

The invention also includes a transfection system for mammalian cells using the constructs described herein. The system uses first and second constructs as described above, although each construct has a disabling mutation in the second selectable marker. The disabling mutations are in different regions of the second selectable marker so that homologous recombination between the two produces a functional product. This system allows for high expression of a desired polypeptide. Mammalian cells modified by the transfection system described herein are also provided, as are methods for making these transfected cells.

Thus, the invention described herein eliminates the tedious process of identification of high expression loci in mammalian cells and provides an efficient mechanism by which any desired polypeptide can be expressed at high levels using the novel cell lines generated as described herein.

Definitions

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA. A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.)

in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra or Ausubel et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamnide, dextran sulfate, and polyethylene glycol), hybridization reaction temperature and time parameters, as well as, varying wash conditions. The selection of a particular set of hybridization conditions is selected following standard methods in the art (see, for example, see Sambrook, et al., supra or Ausubel et al., supra)

A first polynucleotide is "derived from" second polynucleotide if it has the same or substantially the same basepair sequence as a region of the second polynucleotide, its cDNA, complements thereof, or if it displays sequence identity as described above. A first polypeptide is "derived from" a second polypeptide if it is (i) encoded by a first polynucleotide derived from a second polynucleotide, or (ii) displays sequence identity to the second polypeptides as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The terma "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

"Nucleic acid expression vector" or "Expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication). Vector backbones are discussed in further detail below. A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

A "selectable marker" or "reporter marker" refers to a nucleotide sequence included in a gene transfer vector that has no therapeutic activity, but rather is included to allow for simpler preparation, manufacturing, characterization or testing of the gene transfer vector. Suitable selectable markers are discussed further below.

Expression Vectors

In one embodiment, the expression vectors comprise polynucleotides encoding (i) a first crippled, selectable marker; (ii) a product of interest, also referred to as the "transgene"; and (iii) a second, amplifiable selectable marker. By "crippled" is meant a sequence encoding a selectable marker that includes one or more mutations that diminish, but do not destroy, the function of the marker. In one embodiment the first crippled selectable marker is a neomycin resistance ($Neo^r$) sequence in which amino acid residue 182 (Glu) is mutated to Asp. (see, FIG. 2, pESN1.dhfr and Yanofsky et al., infra). In another embodiment, the first crippled selectable marker is a $Neo^r$ sequence in which amino acid residue 261 (Asp) is mutated to Asn (N). (FIG. 2, pESN2.dhfr). In yet another embodiment, the first crippled selectable marker is a $Neo^r$ sequence containing both the above described mutations, e.g., Glu182 to Asp and Asp261 to Sn. (See, FIG. 2, pESN3,dhfr). Other suitable selectable markers and methods of making and testing crippling mutations are described below.

Also included in the expression vectors is a sequence encoding a product of interest (i.e., a "transgene"). Suitable transgenes include polynucleotides encoding for any polypeptide of interest. In one embodiment, the transgene encodes a chimeric protein such as "CAB". CAB combines features of membrane co-factor protein (MTP) and decay accelerating factor (SAF) to inhibit complement activation. See, e.g., Higgins et al. (1997) *J. Immunology* 158(6) :2872–2881. In certain embodiments, the sequence encoding the transgene can also be designed, as described herein, such that aberrant mRNA splicing of the product is reduced or eliminated.

The expression vectors also include a second selectable, amplifiable marker. The second amplifiable marker facilitates selection of those cells which express the transgene at high levels, for example dihydrofolate reductase (DHFR). Suitable markers are discussed in detail below.

The expression vectors of the present invention can be produced following the teachings of the present specification in view of techniques known in the art. Sequences, for example encoding transgenes, may be commercially available, for example, green fluorescent protein (G.P.) is available from Clontech, Palo Alto, Calif., and lucifers is available from Promega, Madison, Wis. Exemplified herein are expression vectors which direct high-level expression of the chimeric protein CAB and expression of HIV proteins. However, it is to be understood that the expression vectors, constructs and methods of the present invention are applicable to high-level expression of any polypeptide of interest.

Another standard source for the polynucleotides used in the invention is, of course, polynucleotides isolated from an organism (e.g., bacteria), a cell, or selected tissue. Nucleic acids from the selected source can be isolated by standard procedures, which typically include successive phenol and phenol/chloroform extractions followed by ethanol precipitation. After precipitation, the polynucleotides can be treated with a restriction endonuclease which cleaves the nucleic acid molecules into fragments. Fragments of the selected size can be separated by a number of techniques, including agarose or polyacrylamide gel electrophoresis or pulse field gel electrophoresis (Care et al. (1984) *Nuc. Acid Res.* 12:5647–5664; Chu et al. (1986) *Science* 234:1582; Smith et al. (1987) *Methods in Enzymology* 151:461), to provide an appropriate size starting material for cloning.

Another method of obtaining the nucleotide components of the expression vectors or constructs is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, $Mg^{2+}$ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

Another method for obtaining polynucleotides is by enzymatic digestion. For example, nucleotide sequences can be generated by digestion of appropriate vectors with suitable recognition restriction enzymes. Restriction cleaved fragments may be blunt ended by treating with the large fragment of *E. coli* DNA polymerase I (Klenow) in the presence of the four deoxynucleotide triphosphates (dNTPs) using standard techniques.

Polynucleotides are inserted into suitable backbones, for example, plasmids, using methods well known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and available in the art. A variety of sources can be used for the component polynucleotides.

Constructs for Transfection Systems

The invention also includes using first and second constructs in particular methods of producing and selecting stably transfected cell lines, particularly mammalian cell lines. In the transfection system described herein, the first construct comprises polynucleotides encoding first and second selectable markers. The first selectable marker is typically under the control of a strong promoter. As described above, the first selectable marker preferably contains at least one crippling mutation. In addition, in these embodiments, the second marker contains a disabling mutation, preferably in the 3' or 5' end of the coding region. By "disabling" is meant a mutation that reduces or, preferably eliminates, a functional gene product.

Figure 4:
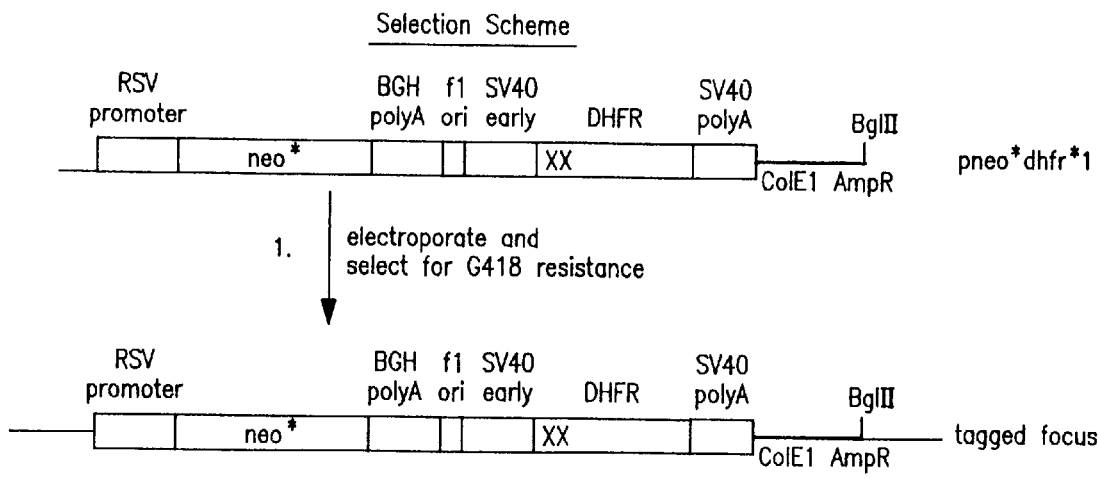
FIG. 4 is a schematic representation of a DNA construct designated pneo*dhfr*1, which comprises a mutant neomycin resistance gene (neo*) and a disabled DHFR marker gene, where XX represent mutations in the DHFR gene.

An exemplary first construct is shown in FIG. 4 and identified as pneo*dhfr*1. The first selectable marker encoded by this construct is an antibiotic resistance marker which imparts resistance to neomycin (neo*), preferably a crippled mutant of neo, designated neo* in the Figures. The neo* gene is operably linked to a strong promoter (e.g., CMV or RSV, shown 3' to the neo* gene), and may be generally linked to other expression regulatory elements such as polyadenylation sequences (e.g., a bovine growth hormone (BGH) polyadenylation site). Further, an origin of replication useful for propagation in a microorganism may also be included (e.g., the f1 ori). The BGH polyA sequence and the f1 origin are typically 5' to the neo* gene.

In this example, the second selectable marker of pneo*dhfr*1 construct encodes, for example, dihydrofolate reductase (DHFR). However, the function of the second selectable marker is disabled. Referring to FIG. 4, XX represent disabling mutations proximate the 5' end of the DHFR gene. The DHFR gene is driven by the SV40 early promoter and, at its 3' end, are sequences coding for SV40 polyA, ColE1, AmpR, and an appropriate restriction site, such as BglIII shown in FIG. 4.

The second vector construct of the transfection system comprises a polynucleotide encoding a heterologous polypeptide of interest (labeled "transgene" in the Figures) and a polynucleotide encoding the same second marker (i.e., the "second" selectable marker)that is used in the first construct. However, in the second construct, the second marker sequence contains a disabling mutation in a different position relative to the first construct, preferably on the opposite end of the coding region. The location of the disabling mutation in the second selectable marker of the first construct, and the location at the disabling mutation in the selectable marker of the second construct, are such that a single recombination event between the two copies of the coding sequences of the selectable marker can generate a functional selectable marker. Once the first construct has randomly integrated into the genome of the host cell homologous recombination events between the integrated first construct and second construct results in insertion of the transgene under the control of the strong promoter. Functional recombinants can be readily selected by assaying for the second marker. Thus, unlike other targeting systems, for example, as described in Detloff et al. (1994) Molecular and Cellular Biology 14:3936–6941, the transfection system described herein does not rely on homologous recombination events to alter the transgene of interest.

Figure 5:
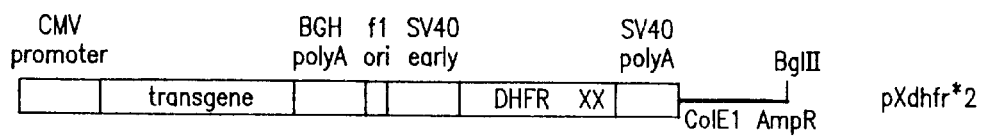
FIG. 5 depicts a vector designated pXdhfr*2, which also carries a transgene and a disabled DHFR gene mutated at a different site as indicated by XX.
Figure 6:
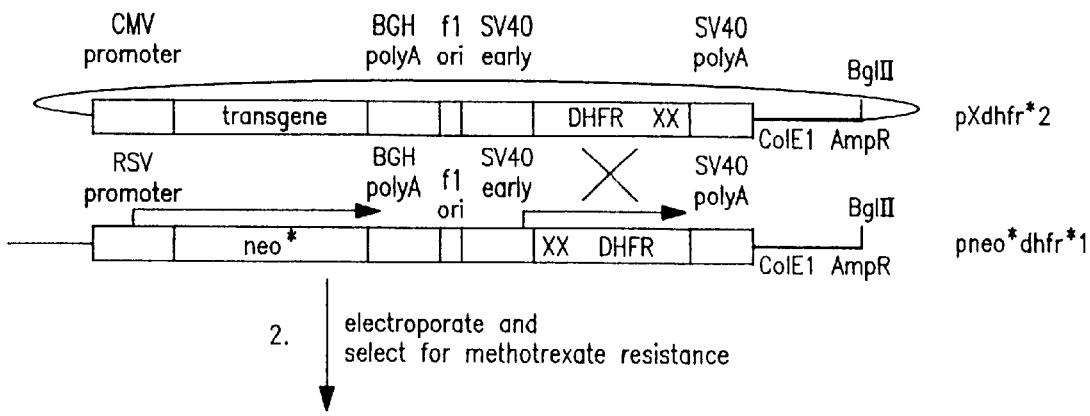
FIG. 6 depicts homologous recombination between pXdhfr*2 and pneo*dhfr*1 at the two copies of the disabled DHFR marker gene.
Figure 10:
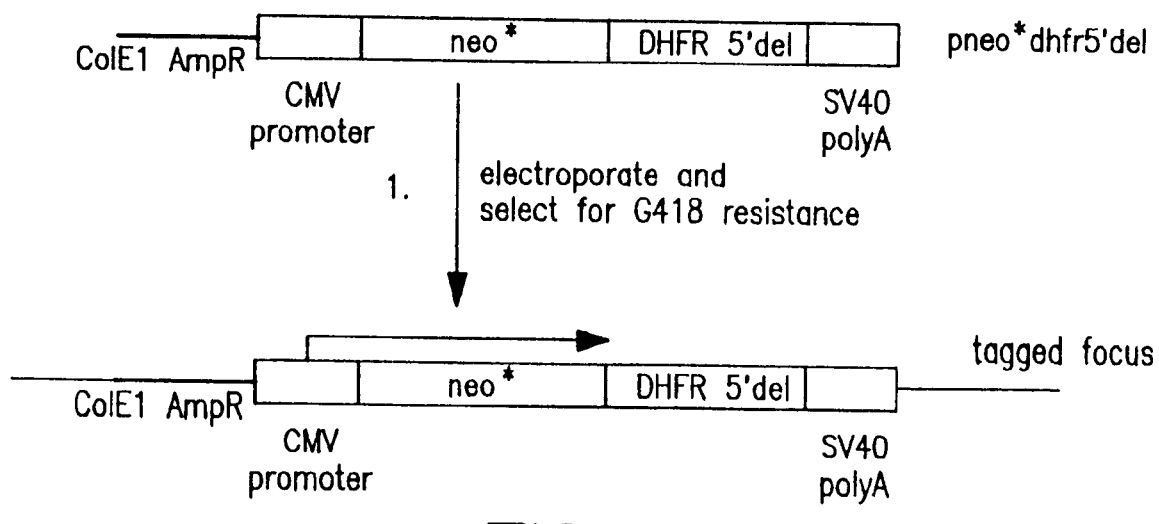
FIG. 10 shows a DNA construct pneo*dhfrS'del (e.g., pneoldhfr5'del, pneo2dhfr5'del, pneo3dhfr5'del) in which a DHFR gene is disabled by 5' deletions and the disabled gene is covalently linked to a mutant neo* gene.

An exemplary second construct is shown in FIG. 5, and is designated pXdhfr*2. Here, the transgene is operably linked to the CMV promoter and includes a 3' BGH polyA tail and f1 origin of replication. The second selectable marker, DHFR, is disabled by mutation(s) at the opposite end of the coding region to the disabled marker in the first construct. Thus, in FIG. 5, the mutations (designated XX) are in the 3' end of the DHFR sequence. As in the pneo*dhfr*1 construct, the disabled DHFR marker is followed by nucleotide sequences encoding SV40 polyA, ColE1, AmpR, and a matching restriction site, in this case BglIII.

First and second constructs for use in transfection systems can be produced following the guidance of the present specification using methods known in the art, for example as described above.

General Methods

The expression vectors and methods described herein are useful in improving expression of a transgene of interest. Stable, high-level expression of genes in mammalian cells is critically dependent on both the site of integration and the copy number. The selection pressure imposed by the usual concentration of the neomycin analog G418, for example, is low and yield cell clones with widely different expression levels. Aberrant splice sites with the transgene may also hamper expression. The expression vectors described herein solve this and other problems by using a crippled first selectable marker operably linked a transgene of interest and a second, amplifiable selectable marker, which, in certain embodiments, contains a disabling mutation. The crippled marker and second marker allow for selection of high-expressing clones. In addition, expression may be increased by altering the transgene such that aberrant slicing is corrected. A strong promoter optionally containing an intron and/or enhancer may also be added to promote expression of the transgene.

The invention also provides a novel transfection system using first and second constructs. These highly efficient methods are capable of generating cells which produce high levels of the desired polypeptide. Cells are transformed with the first construct which integrates randomly into the target cellular genome. Exemplary target cells include, but are not limited to, mammalian cells and call lines (e.g., BHK, VERO, HT1080, 293, RD, COS-7, and CHO cells). The cells are grown in the presence of the appropriate substrate for the first selectable marker, for example, G418 if the first selectable marker encodes neomycin. Cells that survive selection in high concentration of the antibiotic have integrated the neomycin resistance gene at a high expression locus.

The cells having an integrated first construct are then used to make the cell lines of the invention by the following technique. The second construct is introduced into cells carrying an integrated copy of the first-construct. Homologous recombination between the two disabled DHFR genes results in a functional DHFR gene, as well as insertion of the desired gene encoding the functional polypeptide at the high expression locus (see, FIG. 7). Cell lines that survive selection with the appropriate toxin or antibiotic (e.g., methotrexate) have successfully undergone homologous recombination.

The second step can be repeated with any number of variations in the desired gene encoding the functional polypeptide (i.e. transgene) in order to obtain high level expression of the polypeptide of interest. This technique will now be described in greater detail with reference to the Figures.

Transgenes

The transfection system described herein is useful to express any polypeptide of interest. As used herein, the term "transgene" refers to exogenous DNA inserted in the genome of a mammalian cell whose expression at an elevated level in the cell is desired. The transgene employed in this invention encodes a functional polypeptide, which is an amino acid sequence that possesses a biological activity or an amino acid sequence that is a precursor of a protein having a biological activity. The transgene will generally encode a native or recombinant protein, although the expression of other polypeptides, such as epitopes or other immunologically active polypeptides, are contemplated within the scope of this invention. Examples of proteins that can be expressed using the method of this invention are hormones; cytokines, such as growth factors; enzymes; receptors; oncogenes; polypeptide vaccines, viral proteins, and structural and secretory proteins. In one embodiment, the expression vectors contain sequences encoding CAB2, described above. These sequences have been ftirther modified such that aberrant splicing is corrected, see Examples. In another embodiments, the expression vectors contain sequences encoding viral polypeptides, particular derived from HIV. These viral polypeptides include, but are not limited to, envelope (Env) polypeptides (e.g., gp 120, gp160, gp140, gp41, and monomers or multimers thereof), Gag polypeptides (e.g., Gag, Gag-protease, Gag-polymerase), rev, tat, etc. In addition, the expression vectors can include transgenes encoding for synthetic HIV polypeptides, for example constructs described in the Examples.

The transgene employed in the constructs of the invention can be cloned sequences that retain intronic regions. If the exonic structure of the gene is known, the coding exons can be inserted in the constructs.

Expression of the polypeptide of interest can be directed by a promoter homologous to the polypeptide coding sequences (for example, human glucose-6-phosphate dehydrogenase under the control of its own transcription promoter sequences). Further, other homologous or heterologous expression control elements (e.g., affecting transcription, translation, or post-translational events) may be used.

It should be understood that expression of the transgene in the mammalian cells of the invention can be stable or transient. Even transient expression at a higher than normal level is useful for finctional studies in the cells or for the production and recovery of proteins of interest.

Selectable Markers

Any suitable sequence encoding for a selectable marker can be used as the first or second markers in the compositions and methods described herein. Typically, the selectable marker genes employed in this invention can be obtained from readily available sources.

In one embodiment of the invention (depicted in the accompanying Figures), the first selectable marker encodes a gene which confers resistance to antibiotics. For example, in one aspect, the first selectable marker comprises a neomycin (neo) resistance gene. In preferred embodiments, mutant neo genes, designated neo*, can be used to establish a high expression locus in chromosomal DNA of the mammalian calls. (see, e.g., Yanofsky et al. 9(1990) PNAS USA 87:3435–39). The neomycin resistance gene of transposon Tn5 encodes for neomycin phosphotransferase II, which confers resistance to various antibiotics, including G418 and kanamycin. A single base substitution significantly impairs the function of the enzyme. Neo resistance genes used as selectable markers can be identified by restriction enzyme digestion, because base change results in the loss of an XhoII restriction site. See also Blazquez et al., (Molecular Microbiology, (2991) 5(6):1511–1518) for techniques for creating mutant neo genes for use in this invention. The optimum amount of substrate (e.g., G418) needed for selection can be individually determined for each cell line. Other similar selectable markers include, but are not limited to, those listed below.

Temperature-sensitive selectable markers can also be employed in the practice of the invention. For example, temperature-sensitive neo will be nearly wild type in function at non-stringent temperature and have low activity at stringent temperature. After electroporation and initial selection of pneo*ts-dhfr*1, insertion can be performed using G418 at non-stringent temperature, After colonies begin to grow, stringent temperature can be used to kill off colonies carrying low expression insertions.

As described above, the second selectable marker is included to enhance expression. In the expression vectors, the second selectable marker is typically an amplifiable marker, for example, DHFR. DHFR is necessary for purine biosynthesis. In the absence of erogenous purines, this enzyme is required for growth. Methotrexate is a potent competitive inhibitor of DHFR, so increasing methotrexate concentration selects for cells that express increased levels of DHFR. Extremely high levels of expression of the transfected normal DHFR gene are needed for selection in cell lines with high endogenous DHFR levels. To increase expression to even, higher levels, the transgene can be amplified by standard DHFR amplification methods.

For the constructs used in the transfection methods, the second selectable marker is found on both the first and second constructs of the claimed transfection system. However, these copies of the second selectable marker are disabled by mutations in different regions. These mutations are such that homologous recombination between the two mutated copies will rescue function of the gene. In one embodiment, the second (disabled) selectable marker encodes for DHFR.

The disabling mutations to the second selectable marker of the first and second constructs can be introduced by a variety of methods, for example, the DHFR gene or other marker gene can be disabled by the deletion of nucleotides in the native gene sequence or by substitution of nucleotides. Bulleijahn et al. (J. of Bio Chem. (1992) 267:864–870) provide an overview of how the activity of dihydrofolate reductase (DMM) enzyme is affected by residue deletions and/or substitutions. They describe deletions in critical areas (achieved by expressing an altered gene), which result in reduction of activity with complete loss of activity following deletion of 6 amino acids. In addition, a mutant DHFR gene is available that encodes an enzyme resistant to methotrexate (Simonsen et al., (1983) PNAS USA 80:2495–2499).

In some instances, it may also be desirable to amplify the gene encoding the second selectable marker (e.g., DHFR). This can be accomplished, for example, by increasing the concentration of substrate (e.g., methotrexate). Thus, cells harboring copies of the DHFR gene, multiplied many times, can be selected by sequential increases in the concentration of methotrexate to high levels. This technique also makes it possible to identify stable transformants. That is, whereas this phenotype is frequently unstable and is lost after several cell cycles in the absence of selective pressure, the unstable configuration of DHFR genes becomes stable under continuous selective pressure. Stably amplified cells contain the amplified DHFR genes within their chromosomes.

It will be understood that other selectable markers, which permit isolation of stable transfectants, can be employed in this invention as either first or second (disabled) markers. An example of another selectable marker is adenosine deaminase (ADA). A medium supplemented with thymidine, 9-β-D-xylofuranosyl adenine (Xy1-A), and 2'-deoxycoformycin (dCF) is employed. Xy1-A can be converted to Xy1-ATP and incorporated into nucleic acids, resulting in cell death. Xy1-A is detoxified to its inosine derivative by ADA. dCF is a transition state analogue inhibitor of ADA, and is needed to inactivate ADA endogenous to the parental cell type. As the level of endogenous ADA varies with cell type, the appropriate concentration of dCP for selection will vary as well. Kaufman et al., (1986) PNAS USA, 83:3136–3140. ADA-deficient CHO cells are also available.

Another suitable selectable marker for use in the invention is thymidine kinase (TK). In forward selection (TK$^-$ to TX$^+$), complete medium is supplemented with hypoxanthine, aminopterin, thymidine, and glycine (HAT medium). In reverse selection (TK$^+$ to TX$^-$), complete medium is supplemented with 5-bromodeoxyuridine (BrdU). Under normal growth conditions, cells do not need thymidine kinase, because the usual means for synthesizing dTDP is through dCDP. Addition of BrdU to the medium will kill Tk$^+$ cells, as BrdU is phosphorylated by TX and then incorporated into DNA. Selection of TK$^+$ cells in HAT medium is primarily due to the presence of aminopterin, which blocks the formation of dTDP from dCDP. Cells, therefore, need to synthesize dTTP from thymidine, a pathway that requires TK. Thymidine kinase is widely used in mammalian cell culture because both forward and reverse selection conditions exist. Like ADA and DHFR, most mammalian cell lines express TK, removing the possibility of using the marker in those lines unless BrdU is used to select a TK⁻ mutant. See Littlefield et al., (1964)Science 145:709–710.

An example of another suitable dominant selectable marker for use in the invention is xanthine-guanine phosphoribosyltransferase (XGPRT, gpt). Medium containing dialyzed fetal calf serum and xanthine, hypoxanthine, thymidine, aminopterin, mycophenolic acid, and L-glutamine can be employed. Aminopterin and mycophenolic acid both block the de novo pathway for synthesis of GMP. Expression of XGPRT allows cells to produce GMP from xanthine, allowing growth on medium that contains xanthine, but not guanine. XGPRT is a bacterial enzyme that does not have a mammalian homolog, allowing XGPRT to function as a dominant selectable marker in mammalian cells. The amount of mycophenolic acid necessary for selection varies with cell type and can be determined by titration in the absence and presence of guanine. See Mulligan at al., (1981) PNAS USA 78:2072–2076.

The selectable marker hygromycin-B-phosphotransferase (HPH) can also be employed. Complete medium in supplemented with hygromycin-B. Hygromycin-B is an aminocyclitol that inhibits protein synthesis by disrupting translocation and promoting mistranslation. The HPH gene has been used in mammalian systems, and vectors that efficiently express the gene are available. See Gritz et al., (1983)Gene 25:179–188; and Palmer et al., (1987) PNAS USA 84:1055–1059.

Another useful marker is chloramphenicol resistance, Resistance is mediated by chloramphenicol acetyltransferase (CAT), which inactivates chloramphenicol by converting it into mono- and bi-acetylated derivatives. These derivatives can be detected by thin layer chromatography. This enzyme is expressed in mammalian cells and is easily detected because it does not naturally occur in mammalian cells. The gene can be obtained from a derivative of PBR322 carrying transposon Tn9 by cleavage with suitable enzymes. It can be introduced into vector pSV2, yielding plasmid pSV2-cat (ATCC Accession No. 37155) a plasmid expresses the CAT gene from the early promoter of SV40.

Gossen et al., Science (1995) 268:1766–1769, describe fusion of a tetracycline resistance gene repressor to a viral transcription activation domain in order to induce rapid, greatly amplified gene expression in the presence of tetracycline. It is a modification of a preexisting system in which low levels of tetracycline prevented gene expression. The gene that codes for the tetracycline resistance gene repressor was mutagenized and a mutant fusion protein was created that depended on tetracycline for activation was identified. The construct can provide an on/off switch for high expression of a gene.

Another suitable marker is adeninephosphoribosyl transferase (APRT). The enzyme APRT, another enzyme of the purine salvage pathway, catalyzes the conversion of adenine to AMP. APRT positive cells can be selectable in a medium containing, for example, the glutarnine analogue azaserine, which prevents de novo synthesis of purines. APRT-negative cells cannot be grown in a medium containing azaserine and adenine, and can be selected by treatment with 2,6-diaminopurine. This compound is toxic for normal cells, but APRT-negative cells survive because they do not incorporate it.

The expression of the selectable marker coding sequences can be placed under the control of, for example, promoter sequences derived from CMV, RSV, polyA'-BGH, SV40 or the like, and may include other expression control elements as well (e.g., sequences affecting transcription, translation or post-translation modifications).

Regulatory Sequences

In addition to selectable markers and transgenes, the constructs described herein may contain suitable regulatory elements. Regulatory elements (or control elements) are selected for use in the host cell of interest, for example, selectable markers may be included to allow propagation in microorganisms, (e.g., f1 origin of replication and ampicillin resistance encoding sequences). Such regulatory elements include, but are not limited to, transcription promoters, transcription enhancer elements, transcription termination signals, polyadenylation sequences (located 3' to the translation stop codon), sequences for optimization of initiation of translation (located 5' to the coding sequence), translation termination sequences, secretion signal sequences, and sequences that direct post-translational modification (e.g., glycosylation sites). Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

The selectable markers each be sandwiched between the promoter and a polyadenylation site, such as BGH polyA or SV40 polyA as shown in the Figures. A chimeric mRNA is transcribed from the promoters and stabilized by the polyadenylation signals located 3' to the coding regions. During construction of the mammalian transcription unit, any bacterial promoters in the plasmids can be replaced with transcriptional regulatory sequences that are active in animal cells. Two such sequences are shown in the Figures, the CMV promoter and SV40 early promoter. Non-limiting examples of other promoters that can be employed are RSV and HSV-TK.

Ordinarily, gene expression will be constitutive, although regulatable promoters can be employed. Examples of suitable regulatable promoters are Tet, ecdysone and lac repressor sequences. Gene expression can also be controlled by transcription-regulation using heat, light, or metals, such as by the use of metallothionine genes or heat shock genes.

Exemplary "Backbone" Vectors

The above-described components of the transfection system of the present invention can be incorporated into a number of suitable backbone vectors to facilitate manipulation of the expression vectors and constructs. For example, incorporation of the components into a vector containing means that allow replication in a microorganism greatly facilitates propagation and isolation of the constructs (i.e., creating shuttle vectors). Exemplary backbone vectors include, but are not limited to, the following: pCMV6a and pUCl9 (Example 1).

A variety of such backbone vectors are available for appropriate host systems. These systems include, but are not limited to, the following: baculovirus {Reilly, P. R., et al., *BACULOVIRUS EXPRESSION VECTORS: A LABORATORY MANUAL* (1992); Beames, et al., *Biotechniques* 11:378 (1991); Pharmingen; Clontech, Palo Alto, Calif.); pAcC13, a shuttle vector for use in the Baculovirus expression system derived from pAcC12, Munemitsu S., et al., *Mol Cell Biol.* 10(11):5977–5982, 1990}, bacteria {pBR322; Ausubel, F. M., et al., *CURRENT PROTOCOLS IN MOLECULAR BIOLOGY,* John Wiley and Sons, Inc., Media Pa.; Clontech; Promega, Madison, Wis.; Life Technologies, Gaithersburg, MD}, yeast {Rosenberg, S. and Tekamp-Olson, P., U.S. Pat. No. RE35,749, issued, Mar. 17, 1998, herein incorporated by reference; Shuster, J. R., U.S. Pat.

No. 5,629,203, issued May 13, 1997, herein incorporated by reference; Gellissen, G., et al., *Antonie Van Leeuwenhoek,* 62(1–2):79–93 (1992); Romanos, M. A., et al., *Yeast* 8(6):423–488 (1992); Goeddel, D. V., *Methods in Enzymology* 185 (1990); Guthrie, C., and G. R. Fink, *Methods in Enzymology* 194 (1991)}, mammalian cells {Clontech; Promega, Madison, Wis.; Life Technologies, Gaithersburg, Md.; e.g., Chinese hamster ovary (CHO) cell lines (Haynes, J., et al., *Nuc. Acid. Res.* 11:687–706 (1983); 1983, Lau, Y. F., et al., *Mol. Cell. Biol.* 4:1469–1475 (1984); *Methods in Enzymology,* vol. 185, pp537–566. Academic Press, Inc., San Diego Calif. (1991)}, and plant cells {plant cloning vectors, Clontech Laboratories, Inc., Palo Alto, Calif., and Pharmacia LKB Biotechnology, Inc., Pistcataway, N.J.; Hood, E., et al., *J Bacteriol.* 168:1291–1301 (1986); Nagel, R., et al., *FEMS Microbiol. Lett.* 67:325 (1990); An, et al., "Binary Vectors", and others in *Plant Molecular Biology Manual A*3:1–19 (1988); Miki, B.L.A., et al., pp.249–265, and others in *Plant DNA Infectious Agents* (Hohn, T., et al., eds.) Springer-Verlag, Wien, Austria, (1987); *Plant Molecular Biology: Essential Techniques,* P. G. Jones and J. M. Sutton, New York, J. Wiley, 1997; Miglani, Gurbachan *Dictionary of Plant Genetics and Molecular Biology,* New York, Food Products Press, 1998; Henry, R. J., *Practical Applications ofPlant Molecular Biology,* New York, Chapman & Hall, 1997}.

Introduction of Expression Vectors and Constructs

The vectors and constructs described herein can be introduced into suitable host cells by a variety of methods. In particular, the mammalian cells that are modified by the process of this invention can be obtained by transfection or infection with a vector. Transfection can be carried out by well known techniques, such as calcium phosphate transfection, DEAE-dextran mediated transfection, electroporation, liposome mediated transfection, or microinjection (Ausubel, et al., supra). Exemplary methods are also described in the Examples. Transfection can be employed with DNA fragments that are unable to replicate, or with DNA that is not readily packaged in viral vectors, or where infection of the mammalian cells with viral DNA is to be avoided.

Vectors can be derived from viral genomes that yield virions or virus-like particles, which may or may not replicate independently as extrachromosomal elements. Virion particles containing the DNA for the high expression locus can be introduced into the host cells by infection. The viral vector may become integrated into the cellular genome. Examples of viral vectors for transformation of mammalian cells are SV40 vectors, and vectors based on papillomavirus, adenovirus, Epstein-Barr virus, vaccinia virus, and retroviruses, such as Rous sarcoma virus, or a mouse leukemia virus, such as Moloney murine leukemia virus. for mammalian cells, electroporation or viral-mediated introduction can be used. Further usefull delivery systems and vehicles we described herein (see, for example, section 2.3.1.).

Appropriate transformation transfection conditions can be determined by those skilled in the art in view of the teachings herein.

Cells

The cells (e.g., host cells) employed in this invention include all mammalian cells, cell lines, and cell cultures. The cells can be derived from mammals, such as mice, rats, or other rodents, or from primates, such as humans or monkeys. Mammalian germ cells or somatic cells can be employed for this purpose. It will be understood that primary cell cultures or immortalized cells can be employed in carrying out the techniques of this invention.

The mammalian cells are typically grown in cell culture for transformation by the DNA. The cells can be fixed to a solid surface or grown in suspension in appropriate nutrient media.

In the present invention, it is preferred that permanent (i.e., stable) transformation occurs. This is accompanied by integration of the transforming DNA into the cellular genome by recombination. Insertional transformation, which results in the high expression locus being tagged, usually takes place by non-homologous recombination of the DNA construct containing the tag into a random genomic position, although it will be understood that homologous recombination can occur.

It will also be understood that no attempt has been made to determine whether the antibiotic resistance gene and the second selectable marker integrate in a single high expression locus in chromosomal DNA or whether there are multiple sites of integration to form multiple high expression loci in a given cell in any event, the mammalian cells of this invention contain at least one high expression locus.

The transformed cells obtained by the method of this invention can be employed for the preparation of continuous cell lines in which the cells are essentially immortal, or for the preparation of established cell lines that have the potential to be subcultured in vitro. Continuous cell lines and established cell lines can be obtained from a variety of organisms and organs, such as rodent embryos; primate kidneys; rodent and human tumors; and fibroblast, epithelial, or lymphoid cells. Cells exhibiting the highest levels of expression can be cloned, if desired.

Examples of established cell lines that can be transformed by the techniques of this invention are HeLa cells, CV-1 cells, CHO cells, 3T3 cells, L cells, and TC7 cells. All of these cells are sensitive to aminoglyconide antibiotics, such as G418, and are capable of harboring kanamycin or neomycin resistance genes for expression therein.

Moreover, while this invention has been described with reference to expression of a desired finctional polypeptide, it will be understood that the polypeptide need not be the object of the invention. This invention is useful for the production of eucaryotic gene transcription and expression products in general, including RNA.

This invention will be more fully described in the following Examples.

EXAMPLE 1

Constructs pESN1dhfr was constructed as follows. PCR Primers D182E (M1) #1: 5'-GGGTCACGACGAGATCATCGCCGT-3' (SEQ ID NO: 1) and D182 (M1) #2: 3'-CGCATGCCCGACGGCGATGATCT-5' (SEQ ID NO:2) were used to make pcDNA3M1, which contains a mutated neo gene, from pcDNA3 (Invitrogen, Inc.), which contains wild-type neo. Throughout the application, where appropriate, it is noted where primers are presented in 3' to 5' orientation. The PCR fragments were cloned into pCRII for TA cloning. The TA plasmids containing each separate mutation were digested with BssHII and SfuI to remove the region of the neo gene that contained the mutation at amino acid residue 182 (Asp instead of wild-type Glu). pcDNA3M1, containing the neo mutation at residue 182, was created by ligation of the M1 PCR fragment to pcDNA3 digested with BssHII and SfuI. The CMV IE promoter was obtained by digesting pcMV6c with BalI/EcoRV, isolating the fragment and ligating the fragment into pcDNA3M1 digested with the NruI and EcoRV. The resulting plasmid was terms pESN1. To add the Ad-DHFR gene to the plasmid, pESN1 was blunt-ended digested with Bst1107I. The plasmid pmCSR (Chiron Corp.) was digested with XhoI and BamHI and the Ad-DHFR cassette isolated. The cassette was then treated with Klenow, blunt-ended and ligated into the blunt-cut pESN1 to create pESN1.dhfr. pcDNA3M2 was created by ligation of the M2 PCR fragment into pcDNA3 digested with BssHII and SfuI. pcDNA3M3 was created by digestion of pcDNA pESN2dhfr was constructed as follows. Primers D261N (M2) #1: 5'TCCCGCTCAGAAGAACTCGTTAAGAA-3' (SEQ ID NO:3)and D261N (M2) #2: 3'-CTATCGCCTTCTAACGAGTTCT-5' (SEQ ID NO:4) were used to make pcDNA3M2, which contains a mutation in the neo gene at amino acid residue 261 (Asn instead of wild-type Asp). The PCR fragments were cloned into pCRII for TA cloning. The TA plasmids containing each separate mutation were digested with BssHII and SfuI to remove the region of the neo gene that contained the mutation at amino acid residue 182 (Asp instead of wild-type Glu). pcDNA3M2, containing the neo mutation at residue 261, was created by ligation of the M2 PCR fragment to pcDNA3 digested with BssHII and SfuI. The CMV IE promoter was obtained by digesting pcMV6c with BalI/EcoRV, isolating the fragment and ligating the fragment into pcDNA3M2 digested with the NruI and EcoRV. The resulting plasmid was terms pESN2. To add the Ad-DHFR gene to the plasmid, pESN2 was blunt-ended digested with Bst1107I. The plasmid pmCSR (Chiron Corp.) was digested with XhoI and BamHI and the Ad-DHFR cassette isolated. The cassette was then treated with Klenow, blunt-ended and ligated into the blunt-cut pESN1 to create pESN2.dhfr.

pESN3dhfr was constructed as follows. pcDNA3M3 was created by digesting pcDNA3M1 and pcDNA3M2 with SmaI and RsrII. The small fragment from pcDNA3M1 was then ligated to the large fragment of pcDNA3M2 to create pcDNA3M3, which contains mutations at residues 182 and 261 of the neo gene. pESN3.dhfr was created as described above by inserting the CMV IE promoter and DHFR genes.

pneo*dhfr*1 and pneo*dhfr*2 were created as follows. A murine DHFR gene was amplified from pSV2 using primers that create BstBI and StuI ends. The wild type Neor gene was removed from pcDNA3 and replaced with the wild-type murine DHFR gene to create pcDNA3dhfr. This plasmid was then used in PCR to create mutant DHFR genes. For pneo*dhfr*1, two adjacent codons in the 5' region of dhfr (using pSV2dhfr) are replaced with 2 stop codons thereby forming a 5'-mutated DHFR gene. For pneo*dhfr*2, two adjacent codons in the 3' region are replaced with stop codons. The mutations were introduced by PCR amplification of pcDNA3dhfr using the primers shown in Table 1:

TABLE 1

| dhfr primer | Sequence | |
|---|---|---|
| #5 | 3'-CTCGTTCTTGCCAATCCCCTATTA TTGGGACACGGCGACGATGC-5' | (SEQ ID NO:5) |
| #6 | 5'-AGGGAGGCTTTTTTGGAGGCCTAG GCT-3' | (SEQ ID NO:6) |
| #7 | 5'-GCATCGTCGCCGTGTCCCAATAAT AGGGGATTGGCAAGAACGGAG-3' | (SEQ ID NO:7) |
| #8 | 3'-GGCATTCGAAGCATAGCTTTAGGA GGGGAGCAGAG-5' | (SEQ ID NO:8) |
| #9 | 3'-CTCAGAGAGGACGCCTGGCTATTA TGGGAGAAGTTTATATTTCCCC-5' | (SEQ ID NO:9) |

TABLE 1-continued

| dhfr primer | Sequence | |
|---|---|---|
| #10 | 5'-GGGGAAATATAAACTTCTCCCATA ATAGCCAGGCGTCCTCTCTGAG-3' | (SEQ ID NO:10) |

Mutations in the 5' end of the dhfr gene were accomplished using primers #5, #6, #7 and #8. Mutations in the 3' end were accomplished using primers #6, #8, #9 and #10. These new vectors were referred to as pXdhfr*1 and pXdhfr*2, where X refers to any transgene. Mutant forms of the neo resistance gene from pESN1, pESN2 or pESN3 are then inserted into pdhfr*1 or pdhfr*2 to create pneo*dhfr*1 and pneo*dhfr*2. These constructs can be used, as described below, to create a high expression site in a host cell.

pdhfr3'del was constructed as follows. pcDNA3DHFR3' was digested with KpnI/EcoRV. Secreted alkaline protease (SeAP) was obtained by digesting pSeAP-Basic (Clontech) with ClaI, followed by Klenow treatment and digestion with KpnI. The fragment was then ligated into pcDNA3DHFR3' under blunt/sticky conditions. pXdhfr3'del refers to this plasmid containing any transgene "X".

pneo*dhfr5'del was constructed as follows. Plasmid pFC55 (Chiron Corp), which contains the same neo resistance gene from pcDNA3, was digested with BssHII and SfuI to insert the neo mutation fragments obtained as described above. The BssHII/SfuI M1, M2 or M3 neo fragments were ligated into pFC55 to create pRSVM1neo, pRSVM2neo or pRSVM3neo, respectively. pcDNA3dhfr5' (courtesy F. Randazzo) was digested with NruI/KpnI to remove the CMV promoter upstream of the polylinker region. pRSVM1neo was digested with NruI/KpnI and the resulting fragment inserted into pcDNA3dhfr5', creating pRSVM1 neodhfr5'. The resulting plasmid was digested with BssHII and KpnI to insert either RSVM2neo or RSVM3neo fragments.

pCMVKm2: The pCMVKm2 vector was derived from pCMV6a (Chapman et al., Nuc. Acids Res. (1991) 19:3979–3986) and comprises a kanamycin selectable marker, a ColE1 origin of replication, a CMV promoter enhancer and Intron A, followed by an insertion site for the synthetic sequences described below followed by a polyadenylation signal derived from bovine growth hormone— the pCMVKm2 vector differs from the pCMV-link vector only in that a polylinker site was inserted into pCMVKm2 to generate pCMV-link (polylinker at positions 1646 to 1697); pESN2dhfr and pCMVPLEdhfr, for expression in Chinese Hamster Ovary (CHO) cells; and, pAcC13, a shuttle vector for use in the Baculovirus expression system (pAcC13, was derived from pAcC12 which was described by Munemitsu S., et al., Mol Cell Biol. 10(11):5977–5982, 1990).

pCMV-link contains the CMV promoter (CMV IE ENHIPRO), bovine growth hormone terminator (BGH pA), kanamycin selectable marker (kan), and a ColE1 origin of replication (ColE1 ori). A polycloning site is also present following the CMV promoter sequences.

A restriction map for vectors pESNdhfr, pESN1dhfr, pESN2dhfr, pESN3dhfr is presented in FIG. 2. In the figure, the CMV promoter (pCMV, hCMVIE), bovine growth hormone terminator (BGHpA), SV40 origin of replication (SV40ri), neomycin selectable marker (Neo), SV40 polyA (SV40pA), Adenovirus 2 late promoter (Ad2VLP), and the murine dhfr gene (mu dhfr) are indicated. A polycloning site is also indicated in the figure following the CMV promoter sequences.

Briefly, construction of pCMVPLEdhfr was as follows. To construct a DHFR cassette, the EMCV IRES (internal ribosome entry site) leader was PCR-amplified from pCite-4a+(Novagen, Inc., Milwaukee, WI) and inserted into pET-23d(Novagen, Inc., Milwaukee, WI) as an Xba- Nco fragment to give pET-EMCV. The dhfr gene was PCR-amplified from pESN2dhfr to give a product with a Gly-Gly-Gly-Ser (SEQ ID NO:33) spacer in place of the translation stop codon and inserted as an Nco-BamH1 fragment to give pET-E-DHFR. Next, the attenuated neo gene was PCR amplified from a pSV2Neo (Clontech, Palo Alto, CA) derivative and inserted into the unique BamH1 site of pET-E-DHFR to give pET-E-DHFR/Neo$_{(m2)}$. Finally the bovine growth hormone terminator from pCDNA3 (Invitrogen, Inc., Carlsbad, CA) was inserted downstream of the neo gene to give pET-E-DHFR/Neo$_{(m2)}$BGHt. The EMCV-dhfr/neo selectable marker cassette fragment was prepared by cleavage of pET-E-DHFR/Neo$_{(m2)}$BHHt.

The CMV enhancer/promoter plus Intron A was transferred from pCMV6a (Chapman et al., *Nuc. Acids Res.* (1991) 19:3979–3986) as a HindIII-Sal1 fragment into pUC19 (New England Biolabs, Inc., Beverly, Mass.). The vector backbone ofpUC19 was deleted from the Nde1 to the Sap1 sites. The above described DHFR cassette was added to the construct such that the EMCV IRES followed the CMV promoter. The vector also contained an Amp$_r$ gene and an SV40 origin of replication.

pCMVKm2 vectors containing synthetic Gag expression cassettes have been designated as follows: pCMVKm2.GagMod.SF2, pCMVKm2.GagprotMod.SF2, and pCMVKm2.Gagpo1Mod.SF2, as described in co-pending application Atty Docket Number 1621.002.

CAB constructs: All of the constructs described were made and cloned into pAcC13 in the following manner. Since the CAB2 portion of all constructs was generated by PCR all were sequenced confirmed by the ABI system of dye terminator sequence analysis. Initially all constructs were cloned into the intermediate cloning vectors PCRII by INVITROGEN or pBluescript SK+ by Stratagene. This was done for ease of sequencing and further subcloning.

All CAB2 constructs were generated in two parts. First the MCP portion of the CAB2 molecule from the KpnI site at the 5' end to the HindIII site at amino acid 321 was generated and cloned into PCRII and analyzed to confirm correct sequence. This portion of CAB2 was then cloned into pBluescript SK+. Then into this SK+ construct the remaining portion of CAB2, from the HindIII site at amino acid 321 to the 5' end EcoRI site, including the various 3' end tails was cloned. The primers used to generate the HindIII 5' and 3' ends were:

CAB2H3-1 CAGAAAGCTTTCTTCACATTTGTACGT-TATTAC (SEQ ID NO: 11)

DAFTH5-1 CAGAAAGCTTTGTGAAAATTCCTGGC-GAGAAGGAC (SEQ ID NO:12)

The original HindIII to EcoRI PCR products containing the Short Heparin consensus, the TFPI heparin consensus, and the GPI tail were initially cloned into PCRII for sequence analysis. The original HindIII to EcoRI PCR products containing the Long Heparin consensus, the two fibronectin tails, and the control sequence with no tail were cloned into pBluescript SK+ for sequence analysis. After combining the two halves to make the complete CAB2 in SK+ for each of the variants the KpnI to EcoRI fragments were then subdloned into pAcCI3. All were expressed in insect cells using the Baculovirus system.

In addition to insect cell expression some of these constructs were generated for expression in mammalian systems. They include CAB2 with the Long Heparin Consensus sequence, the TFPI Heparin binding tail, and the control with no targeting sequence. All three of these CAB variants were again generated with PCR in order to change the 5' and 3' restriction sites required for cloning into mammalian system vectors. All variants were generated with 5' end Not I and 3' end Xba I sites and cloned into the intermediate vector PCRII for sequence confirmation. The PCR primers used to generate Not I to Xba I clones were identical to those used to generate the KpnI to EcoRI fragments except for the change in restriction site. Confirmed variants were then cloned into pGEM9Z (Promega). These were then transferred to a mammalian vector for expression.

EXAMPLE 2

Identification and Correction of Aberrant mRNA Splicing

Cab2 is a chimeric, 110 kDa protein that combines features of membrane cofactor protein (MCP) and decay accelerating factor (DAF) to inhibit complement activation. Higgins et al., supra. Initially, a CHO cell line (N2107) was established after transfection of a pcDNA3 vector (Invitrogen) carrying a sequence encoding CAB2.1. However, the productivity of this cell line was low and, further, declined over time.

Analysis of the polypeptides present in the supernatant of the N2107 cell line revealed a 42 kDa protein having unexplained CAB2.1-related sequence. Poly (A+) mRNA was isolated from cell pellets of cells transiently transfected with CAB2-containing plasmids using Fast Track (InVitrogen). RT-PCR analysis was conducted as described in the Perkin-Elmer RT-PCR kit using primers which flank the coding region. The predominant PCR product encoded a predicted protein of 42 kDa. Also present were several intermediate PCR products and a small amount of full-length (110 kDa) PCR product. Thus, RT-PCR revealed that the 42 kDa contaminant was caused by aberrant mRNA splicing between the chimeric domains of MCP and DAF in CAB2.1.

Aberrant splicing was corrected by overlapping PCR to produce splice-corrected sequences of CAB2.1, CAB4.2 and CAB4.3, by removing donor and acceptor sites for RNA splicing which gave alternate protein side processed product from mammalian cell in such a way as to preserve the amino acid so that it no longer resembled the consensus splicing. The changes were as follows:

| Donor Sites: | Original Codons | New Codons |
|---|---|---|
| amino acids 47–48 (Ile-Gly) | ATT GGT | ATC GGG |
| aa 152 153 154 155 (Gly-Lys-Pro-Pro: SEQ ID NO:13) | GGT AAG CCA | GCA AAA CCC |

-continued

| Acceptor Sites: | Original Codons | New Codons |
|---|---|---|
| amino acids 372 373 374 (Tyr-Phe-Pro SEQ ID NO:14) | TAT TTT CCA | CTT ATT TCA AGC TCT (SEQ ID NO:15) |
| aa 459 460 461 462 463 464 (Leu Ile Ser Gly Ser Ser SEQ ID NO:16) | TAC TTC CCT | CTA ATA AGC TCG AGT (SEQ ID NO:17) |

The changes were generated using overlapping PCR with the following primers. To change the Donor site starting at amino acid 47:

SACOL5P 5'-TATGGAGCTCATCGGGAAACCAAAA (SEQ ID NO:18)

SACOL3P 3'-GGGTTTTGGTTTCCCGATGAGCTC (SEQ ID NO:19)

To change the Donor site starting at amino acid 152:

NDE3P 3'-TTCACATATGGGGGGTTTTCCGCT (SEQ ID NO:20)

NDE5P 5'-AGCGGAAAACCCCCCATATGTGAA (SEQ ID NO:21)

To change the Acceptor site starting at amino acid 372:

ACCOL5P 5'-ATCACTCAGAATTACTTCCCTGTCGGT (SEQ ID NO:22)

ACCOL3P 3'-AACAGTACCGACAGGGAAGTAATTCTG (SEQ ID NO:23)

To Change the Acceptor site starting at amino acid 459:

ACCXH05P 5'-AATAAGCGGCTCGAGTGTCCAGTGG (SEQ ID NO:24)

ACCXH03P 3'-GACACTCGAGCCGCTTATTAGACA AAA (SEQ ID NO:25)

The 5'Kpn primer used was:

MCPK5-2 5'-CAGAGGTACCATGGAGCCTCCCGGC CGCCGCGAG-(SEQ ID NO:26)

The 3'XbaI primer used was;

DAFSXB32 3'-CAAATCTAGATTATCAACGGGTAG TACCTGAAGTGGTTC (SEQ ID NO:27)

Also used were the Hind III 5' and 3' primers named above.

Splice site deleted constructs included the complete CAB2, CAB2 with the TFPI Heparin binding tail, CAB2 with the partial and complete deletion of the Serine Threonine region to amino acid 570 and 561 respectively, and complete deletion of the serine threonine region with addition of the TFPI heparin consensus sequence.

The primers used for generating the Serine Threonine deletions at the 3' end of the molecule were:

STTDELE3: CAGAGAATTCTCATGTTGGTGGGAC-CTTGGA (SEQ ID NO:28)

STDELE31: CAGAGAATTCTCATTTTCCTCTGCATT CAGGAC (SEQ ID NO:29)

CAB4-33P:

CAGAGAATTCTCACATATTTTAACAAAAATTT CTTCATATGCTATTTTCACTCTCTGCTTC TTTC TTTTTCTTTTGGTTTTTTTCCTCTGCATTCAGGTGG TGG (SEQ ID NO:30)

The constructs were made in two parts in the intermediate vector pBluescript SK+ as was done with the original CAB variants. All sequences were confirmed in SK+ before completion of the final constructs in mammalian expression vectors. mRNA analyzed by RT-PCR and by Northern blotting showed no aberrant splicing and bands of the correct size.

EXAMPLE 3

Transfections

Splice-corrected CAB2.1 and CAB4.2 were transiently transfected into COS-7 cells using the LipofectAMINE reagent (BRL) for two hours. RT-PCR showed only the correct full-length PCR product (110 kDa). Levels of CAB protein expressed in these cells are shown in Table 2.

TABLE 2

| Expression Plasmid | CAB 2 conc. (ng/mL) |
|---|---|
| pESN3/CAB2.1C#8.2 | 733 |
| pESN3/CAB2.1C#8.2 | 614 |
| pcDNA3/CAB2.1 | <9.0 |

EXAMPLE 4

Transfection and Selection Methods

The following four transfection protocols of plasmids pESN1.dhfr.CAB2.1; pESN3.dhfr.CAB2.1, pESN1.dhrf.CAB42. or pESN3.dhfr.CAB4.2 were conducted: (1) electroporation; (2) calcium phosphate (CaPo4) (Life Technologies, Gaithersburg, Md.); (3) LipofectAMINE (Life Technologies, Gaithersburg, Md.); and (4) TransIT LT-1 reagent (PanVera Corp., Madison, Wis.). Transfections were conducted according to the manufacturer's instructions for all methods except electroporation. Approximately 3×10$^6$ cells were used per electroporation, and 50–80% confluent cells (5–8×10$^5$ cells) for the three other transfection methods.

Electroporation was conducted as follows. CHO-DIFRF$^-$ cells were tyrpsinized with STV and media with 10% FBS was added to quench the reaction. Cells were washed twice with DMEM (with L-glutamine) and resuspended to approximately 6×10$^6$ cells/mL. 500 μl of cells was added to a sterile cuvette and between about 1–30 μg of DNA added. The cells were electroporated at 330 volts and 975 μFarads capacitance. The cells were plated into 15 mls of α-MEM/ nonselective media (containing G418) in a 100 mm dish, incubated for 18–24 hours at 37° C. Media was then replaced with α-MEM selective medium for DBFR and the cells grown until colonies formed. Cells are replated (T75 flasks, 96 well plates or 100 mm dish) and cultured in 20 nM methotrexate for 2–4 weeks at which point the concentration of methotrexate was raised to 40 nM methotrexate.

Approximately 10 μg of plasmid DNA was used per transfection. Transfected cells were COS (UCSF) or DG44

DHFR-CHO cells (Chiron Corp). After transfection, the cells were allowed to recover in non-selective media (500 mL of non-selective media contains 431.5 mL of α-MEM, 50 mL FBS, non-dialyzed, 5 mL penicillin-streptomycin, 0.5 mL gentamicin, 10 mL glutamine, 1 mL thymidine, 1 ML adenosine and 1 mL deoxyadenosine) for 1–2 days. The cells from one transfection were trypsinized as described above, diluted into 20 mL of selective medium (500 mL of selective media contains 434.5 α-MEM, 10 mL glutamine, 0.5 mL gentamicin, 5 mL penicillin-streptomycin, and 50 mls FBS non-dialyzed) and plated into one 96-well culture plate in appropriate selection media, either 250 μg G418 (Gibco-BRL), α-MEM without nucleosides, 10% FBS (DHFR selection) or both media. Cells were maintained in the selective media for approximately 2–3 weeks, at which time untransfected or transiently transfected cells were dead. Surviving colonies were trypsinized and replaced into 24-well culture plates containing 1 mL of selective media.

Growth-positive wells were tested for expression of CAB2.1 or CAB4.2 using ELISA. CAB2.1 or CAB4.2 expressing mini-pools were scaled-up for DHFR selection and amplification with methotrexate (MTX). Results obtained indicated that CaPO4 was the most effective in obtaining stable expression of the transgene.

The expression of CAB2.1 or CAB4.2 in DHFR-CHO cells is shown in Table 3.

TABLE 3

| Construct | CAB2.1 (in pESN3dhfr) | CAB4.2 (in pESN3dhfr) |
|---|---|---|
| No. of transfections | 8 | 3 |
| No. wells screened | 3360 | 480 |
| No. selected in 24 wells/ range of expression | 237 <0.50–4.10 μg/mL | 118 0.035–5.50 μg/mL |
| No. amplified in T75 flasks/range of expression | 11 0.015–210 μg/mL | 19 0.494–2.33 μg/mL |
| MTX amplification/ range of expression | 1 50.0–106.0 μg/mL | 2 20.0–75.0 μg/mL |
| Selected for cloning | 1 | not determined |

In addition to CAB2, expression of uPAR and VEGF-D has also been achieved by calcium phosphate transfection of host cells with pESN2dhfr containing a transgene coding for uPAR or VEGF-D. Expression levels between about 250 mg to about 1 mg/liter have been achieved.

Deposits of Strains Useful in Practicing the Invention

A deposit of biologically pure cultures of the following strains was made with the American Type Culture Collection (ATCC), 10801 University Boulevard, Manassas, Va. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 U.S.C. §122 and the Commissioner's rules pursuant thereto (including 37 C.F.R. §1.12). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

| Plasmid, Chiron Deposit Number | Date Sent to ATCC | ATCC Accession Number |
|---|---|---|
| pneo3dhfr5'del, CMCC #5090 | November 30, 1999 | PTA-998 |
| pneo1dhfr5'del, CMCC #5089 | November 30, 1999 | PTA-1001 |
| pESN2dhfr, CMCC #5086 | November 30, 1999 | PTA-1002 |
| pdfr3'del, CMCC #5093 | November 30, 1999 | PTA-1003 |
| pneo2dhfr5'del, CMCC #5088 | November 30, 1999 | PTA-1004 |
| pESN1dhfr, CMCC #5085 | November 30, 1999 | PTA-1005 |
| pESN3dhfr, CMCC #5087 | November 30, 1999 | PTA-1006 |

The principles, preferred embodiments and modes of operation of the present invention have been described in the foregoing specification. The invention to be protected herein, however, is not to be construed as limited to the particular forms disclosed, since these are to be regarded as illustrative rather than restrictive. Variations and changes may be made by one of ordinary skill in the art without departing from the spirit of the invention.

What is claimed is:

1. A transfection system comprising
   (a) a first construct comprising, in a suitable backbone, a sequence encoding a functionally impaired selectable marker polypeptide and a sequence encoding a second selectable marker, wherein the second selectable marker contains at least one disabling mutation in its coding sequence; and
   (b) a second construct comprising, in a suitable backbone, a polynucleotide sequence of interest and a sequence encoding a third selectable marker, wherein the third selectable marker is the same selectable marker as the second selectable marker except that the third selectable marker contains at least one disabling mutation that is in a different region of the coding sequence than the disabling mutation in said second selectable marker.

2. The transfection system of claim 1, wherein said functionally impaired selectable marker encodes for antibiotic resistance.

3. The transfection system of claim 1, wherein said functionally impaired selectable marker encodes neomycin phosphotransferase II.

4. The transfection system of claim 1, wherein the second selectable marker in the first construct is disabled by at least one mutation in the 5' coding region and the third selectable marker in the second construct is disabled by at least one different mutation in the 3' coding region.

5. The transfection system of claim 1, wherein said mutations are deletions.

6. The transfection system of claim 1, wherein said second and third selectable markers encode dihydrofolate reductase (DHFR).

7. The transfection system of claim 1, wherein the constructs are plasmids.

8. The transfection system of claim 4, wherein said mutations are point mutations.

9. The transfection system of claim 7, wherein the plasmids further comprise
   (c) first , second , and third promoters operably linked to said functionally impaired and second selectable markers and to a transgene, respectively;
   (d) sequence encoding polyadenylations sites operably linked to said functionally impaired and second selectable markers and said transgene; and
   (e) sequence encoding origins of replication operably linked to said functioncally impaired, second selectable markers and said transgene.

10. The transfection system of claim 9, wherein said first promoter is selected from the group consisting of a cytomegalovirus (CMV) promoter, a respiratory syncytial virus (RSV) promoter and a simian virus 40 (SV-40) early promoter.

11. The transfection system of claim 9, wherein said second promoter is selected from the group consisting of a cytomegalovirus (CMV) promoter, a respiratory syncytial virus (RSV) promoter and a simian virus 40 (SV-40) early promoter.

12. The transfection system of claim 9, wherein said third promoter is selected from the group consisting of a cytomegalovirus (CMV) promoter, a respiratory syncytial virus (RSV) promoter and a simian virus 40 (SV-40) early promoter.

13. The transfection system of claim 9, wherein said first and third promoters are CMV promoters and said second promoter is an SV40 early promoter.

14. A method for producing a mammalian cell line for ecpresssion of a selected polynucleotide sequence, comprising
   (a) introducing into a selected mammalian cell, having a genome, a first contruct comprising a sequence encoding a first selectable marker and a sequence encoding a second selectable marker, wherein the second selectable marker contains at least one disabling mutation in its coding sequence,
   (b) selecting for a mammalian cell expressing the first selectable marker, wherein said first construct stably integrates into the genome;
   (c) introducing into the mammalian cell a second construct comprising the selected polynucleotide sequence and a sequence encoding a third selectable marker, wherein the third selectable marker is the same selectable marker as the second selectable marker except that the third selectable marker contains at least one disabling mutation that is in a different region of the coding sequence than the disabling mutation in said second selectable marker; and
   (d) selecting for a mammalian cell expressing a functional product encoded by the second selectable marker, wherein the functional product is encoded by a sequence produced by a recombination event between said second and third selectable markers, and the resulting mammalian cell is capable of expressing the selected polynucleotide sequence.

15. The method of claim 14, wherein said selected polynucleotide sequence encodes a polypeptide.

16. A mammalian cell produced by the method of claim 14.

17. The method of claim 15, wherein expressing the selected polynucleotide sequence results in expression of the polypeptide.

18. A method for producing a polypeptide of interest in a host mammalian cell, said method comprising:
   (a) introducing into said cell, having a genome, a first construct comprising a sequence encoding a first selectable marker and a sequence encoding a second selectable marker, wherein the second selectable marker contains at least one disabling mutation in its coding sequence;
   (b) selecting for a mammalian cell expressing the first selectable marker, wherein said first construct stably integrates into the genome;
   (c) introducing into the mammalian cell a second construct comprising a polynucleotide sequence encoding the polypeptide of interest and a sequence encoding a third selectable marker, wherein the third selectable marker is the same selectable marker as the second selectable marker except that the third selectable marker contains at least one disabling mutation that is in a different region of the coding sequence than the disabling mutation in said second selectable marker;
   (d) selecting for a mammalian cell expressing a functional product encoded by the second selectable marker, wherein the functional product is encoded by a sequence produced by a recombination event between said second and third selectable markers, and the resulting mammalian cell is capable of expressing the polypeptide of interest; and
   (e) culturing the mammalian cell under conditions to produce the polypeptide of interest.

19. The method of claim 18 wherein said first selectable marker encodes for neomycin resistance.

20. The method of claim 18, wherein said second and third selectable markers encode dihydrofolate reductase (DHFR).

21. The method of claim 18, wherein introduction of said constructs into said cell is by electroporation.

22. The method of claim 18, wherein introduction of said constructs into said cell is by calcium phosphate transfection.

23. A mammalian cell line that produces a polypeptide of interest, wherein said cell line is produced according to the method of claim 18.

* * * * *